(12) United States Patent
Taunton et al.

(10) Patent No.: US 8,748,601 B2
(45) Date of Patent: *Jun. 10, 2014

(54) SELECTIVE SERINE/THREONINE KINASE INHIBITORS

(75) Inventors: Jack Taunton, San Francisco, CA (US); Michael Cohen, San Francisco, CA (US); Kevan Shokat, San Francisco, CA (US); Chao Zhang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 789 days.

This patent is subject to a terminal disclaimer.

(21) Appl. No.: 12/088,059
(22) PCT Filed: Sep. 26, 2006
(86) PCT No.: PCT/US2006/037699
§ 371 (c)(1),
(2), (4) Date: Jul. 29, 2008
(87) PCT Pub. No.: WO2007/038613
PCT Pub. Date: Apr. 5, 2007

(65) Prior Publication Data
US 2009/0221614 A1    Sep. 3, 2009

Related U.S. Application Data

(63) Continuation-in-part of application No. 10/552,847, filed as application No. PCT/US2004/011297 on Apr. 12, 2004.

(60) Provisional application No. 60/462,554, filed on Apr. 11, 2003, provisional application No. 60/720,902, filed on Sep. 26, 2005.

(51) Int. Cl.
*C07D 487/00* (2006.01)
*C07D 411/02* (2006.01)
*C07D 487/04* (2006.01)

(52) U.S. Cl.
CPC .................... *C07D 487/04* (2013.01)

USPC .............................. 544/280; 548/468

(58) Field of Classification Search
CPC ........................................ C07D 487/04
USPC .............................. 544/280; 548/468
See application file for complete search history.

(56) References Cited

U.S. PATENT DOCUMENTS

6,664,252 B2    12/2003   Castelhano et al.
7,687,506 B2 *  3/2010    Taunton et al. ............ 514/265.1

(Continued)

OTHER PUBLICATIONS

Burchat AF, Calderwood DJ, Hirst GC, Holman NJ, Johnston DN, Munschauer R, Rafferty P, and Tometzki GB, "Pyrrolo[2,3-d]pyrimidines containing an extended 5-substituent as potent and selective inhibitors of lck II," Bioorganic and Medicinal Chemistry Letters, Oct. 2000, 10(19), 2171-2174.*

(Continued)

*Primary Examiner* — Paul Zarek
(74) *Attorney, Agent, or Firm* — Kilpatrick Townsend & Stockton LLP

(57) ABSTRACT

Inhibition of protein kinases having one or more cysteine residues within the ATP binding site is effected by contacting the kinase, per se or in a cell or subject, with an inhibitory-effective amount of a compound having a heterocyclic core structure comprised of two or more fused rings containing at least one nitrogen ring atom, and an electrophilic substituent that is capable of reacting with a cysteine residue within the ATP binding site of a kinase. Preferred compounds include certain pyrrolopyrimidines and oxindoles having such an electrophilic substituent and optionally an aromatic or heteroaromatic substituent that is capable of interacting with a threonine or smaller residue located in the gatekeeper position of the kinase. Kinases lacking such cysteine residues may be engineered or modified so that they are capable of being inhibited by such compounds by replacing a valine or other amino acid residue within the ATP binding site by a cysteine residue.

33 Claims, 11 Drawing Sheets

(56) References Cited

U.S. PATENT DOCUMENTS

| | | | |
|---|---|---|---|
| 8,034,821 B2 * | 10/2011 | Taunton et al. | 514/265.1 |
| 2005/0165029 A1 | 7/2005 | Patel et al. | |
| 2007/0082884 A1 * | 4/2007 | Taunton et al. | 514/212.07 |

OTHER PUBLICATIONS

Cohen MS, Zhang C, Shokat KM, and Taunton J, "Structural bioinformatics-based design of selective, irreversible kinase inhibitors," Science, May 2005, 308(5726), 1318-1321.*

Lee, Francis S. et al.; "Distinctive features of Trk neurotrophin receptor transactivation by G protein-coupled receptors"; 2002, *Cytokine & Growth Factor Reviews*, vol. 13, pp. 11-17.

Sexl, Veronika et al.; "Stimulation of the Mitogen-activated Protein Kinase via the $A_{2A}$-Adenosine Receptor in Primary Human Endothelial Cells"; 1997, *The Journal of Biological Chemistry*, vol. 272, No. 9, pp. 5792-5799.

Non-Final Office Action for U.S. Appl. No. 12/088,059. Mailed Jun. 21, 2013. 8 pages.

David S. Waugh, "Making the most of affinity tags," TRENDS in Biotechnology, Jun. 2005, 5 pages, vol. 23 No. 6, published by Elsevier, www.sciencedirect.com.

Milton T.W. Hearn and Danilo Acosta, "Applications of novel affinity cassette methods: use of peptide fusion handles for the purification of recombinant proteins," Journal of Molecular Recognition, Oct. 2001, J. Mol. Recognit. 2001;14: 323-369, John Wiley & Sons, Ltd.

K. Terpe, "Overview of tag protein fusions: from molecular and biochemical fundamentals to commercial systems," Appl Microbiol Biotechnol (2003) 60:523-533, published online: Nov. 7, 2002 by Springer-Verlag 2002.

Varun Shastri, Encyclopedic Dictionary of Biotechnolory 15, Grant Publishing House, vol. 1 2005.

\* cited by examiner

SELECTIVE SERINE/THREONINE KINASE INHIBITORS

CROSS-REFERENCE TO RELATED APPLICATIONS

This application is a National Stage of International Application No. PCT/US2006/037699 filed Sep. 26, 2006 and is a continuation-in-part of application Ser. No. 10/552,847 filed Oct. 11, 2005, which is a National Stage application of PCT/US2004/011297 filed Apr. 12, 2004, which in turn claims the benefit of U.S. provisional patent application 60/462,554 filed Apr. 11, 2003. This application also claims the benefit of U.S. provisional application 60/720,902 filed Sep. 26, 2005. The entire contents of all of the aforesaid applications are hereby incorporated herein.

STATEMENT AS TO RIGHTS TO INVENTIONS MADE UNDER FEDERALLY SPONSORED RESEARCH AND DEVELOPMENT

This invention was made with government support under grant nos. AI44009 and GM71434 awarded by the National Institutes of Health. The Government has certain rights in the invention.

BACKGROUND OF THE INVENTION

Phosphorylation of serine, threonine, and tyrosine residues is a major mechanism for regulating protein function in eukaryotic cells. Protein kinases, the enzymes that catalyze these reactions, regulate all aspects of cell physiology and have thus emerged as therapeutic targets for a variety of human diseases. Small-molecule inhibitors of the Abelson tyrosine kinase (Abl) and the epidermal growth factor receptor (EGFR), for example, have been developed into clinically useful anti-cancer drugs. In addition to providing potential drug leads, selective inhibitors promise to increase the understanding of the cellular roles of protein kinases, most of which are poorly understood. Nearly all kinase inhibitors target the highly conserved adenosine triphosphate (ATP) binding site. Because the ATP binding sites are structurally similar even in divergent kinase domains, the rational design of inhibitors that selectively target even a subset of the ~500 human kinases is a daunting challenge.

One attribute that makes protein kinases attractive drug targets is their ATP-binding site, a deep, hydrophobic cleft at the interface of two conserved subdomains. Many small molecules have been discovered that bind to this site with high affinity. However, because the ATP-binding sites of all protein kinases are highly similar, it has been difficult to design selective inhibitors that specifically target one or a few of the 500 human protein kinases.

The Rsk serine/threonine protein kinases have critical functions in the Ras/MAP kinase signaling pathway, a pathway which is deregulated in many human cancers. Of the four Rsk isoforms (Rsk1-4), Rsk1 and Rsk2 are the best characterized. Rsk1 and Rsk2 are directly activated by the MAP kinases, ERK1 and ERK2. Known substrates of Rsk1,2 include transcription factors involved in cell growth and differentiation (e.g. CREB, c-fos, estrogen receptor) and apoptosis (NF-κB). Rsk1,2 have thus been implicated in transcriptional control downstream of Ras and ERK1,2.

Rsk1-4 are unusual protein kinases in that they have two kinase domains, the NTD ($NH_2$-terminal domain) and the CTD ($CO_2H$-terminal domain). All Rsk substrates that have been characterized thus far are phosphorylated by the NTD. Downstream signaling by the NTD requires at least three sequential phosphorylation events: (1) phosphorylation of the CTD activation loop (T573) by ERK1,2; (2) intramolecular phosphorylation of a linker region (S380) by the CTD, which creates a docking site for the kinase PDK1; (3) phosphorylation of the NTD activation loop (S221) by PDK1.

BRIEF SUMMARY OF THE INVENTION

This invention relates generally to the inhibition of protein kinases, and includes inhibitors that specifically target certain protein kinases, as well as the engineering or modification of proteins so as to be susceptible to inhibition by such inhibitors. For example, this invention provides for the modification of proteins for which inhibitors have not yet been identified so that that inhibition of such proteins may be conducted, and the functioning of kinases in signaling networks can be studied and elucidated. By "inhibiting" or "inhibition" is meant negatively affecting the activity of the kinase in question, at least in part, e.g., partially or totally blocking stimulation, decreasing, preventing, or delaying activation, or inactivating, desensitizing, or down-regulating signal transduction.

In one aspect, this invention relates to certain classes of novel compounds that inhibit one or more of the protein kinases referred to herein. These compounds have a heterocyclic core structure comprised of two or more fused rings containing at least one nitrogen ring atom and contain an electrophilic substituent that is capable of forming a covalent bond with a cysteine residue within the ATP binding site of the kinase. Optionally the inhibitors may contain a second group that is capable of interacting with a threonine or smaller residue that is located in the gatekeeper position. This aspect also includes novel pharmaceutical or therapeutic compositions containing effective kinase-inhibitory amounts of such compounds.

In another aspect this invention relates to a method of inhibiting (preferably inhibiting by formation of a covalent bond that is either reversible or irreversible, and most preferably irreversible) a protein kinase that has one or more cysteine residues within its ATP binding site, comprising contacting the kinase with an inhibitory-effective amount of a compound as described herein. In the case of using the compounds for treatment of a condition, this would involve administering an inhibitory-effective amount of such a compound (or a composition containing such a compound) to a subject (preferably a mammalian subject).

In yet another aspect this invention relates to a method for inhibiting the morphological transformation of a cell in which such a kinase is expressed by contacting the cell or the kinase with an inhibitory-effective amount of a compound as described herein. In yet another aspect this invention relates to a method for inhibiting proliferation of tumor cells. Rsk-family kinases have been shown to prevent apoptosis in melanoma cells (Eisenmann et al., *Cancer Research* (2003), 63: 8330-8337) and leukemia cells (Shimamua et al., *Current Biology* (2000), 10: 127-135). Inhibition of Rsk in these cancer cell lines by introduction of plasmids encoding dominant interfering mutants of Rsk1 or Rsk2 causes apoptosis, also known as programmed cell death. Thus, small molecule inhibitors of Rsk kinase activity, such as described in this invention, are also expected to induce apoptosis in these and other tumor cell lines.

In still another aspect this invention involves the engineering or modification of a protein kinase by replacing an amino acid residue, preferably a valine residue, within the ATP binding site of the protein kinase with a cysteine residue. This can render the enyzmatic activity of the modified protein kinase susceptible to inhibition by the compounds disclosed herein.

In a further aspect, this invention involves the engineering or modification of a protein kinase that contains a cysteine in the ATP-binding site corresponding to Cys436 of human Rsk2. These kinases include Rsk3, Msk1-2, Plk1-3, MEKK1, and Nek2. The engineering or modification of the protein kinase is achieved by replacing a methionine, leucine, isoleucine, lysine, arginine, tryptophan, glutamine, asparagine, proline, tyrosine, histidine, glutamic acid, aspartic acid, valine, or phenylalanine residue in the gatekeeper position of the ATP binding site with a smaller residue, e.g. a threonine, serine, alanine, or glycine residue corresponding to Thr493 of human Rsk2. This can render the kinase susceptible to inhibition by some compounds of this invention, and serve to identify such compounds. Engineering or modification of a protein kinase can transform a kinase that has no known inhibitors (or that can be only inhibited reversibly) into one that for the first time can be inhibited (or can be inhibited irreversibly), for example by compounds of this invention. The now modified kinase can be used to elucidate kinase functioning in signaling networks, for example by being introduced into genetically transformed animals.

In other aspects the invention relates to methods for screening candidate compounds for activity as inhibitors of such kinases or for various therapeutic or pharmaceutical properties or activities to which inhibition of a kinase activity may be relevant, for example for pre-screening or screening compounds for anti-cancer activity; to libraries such as combinatorial libraries containing compounds that either have been found to be inhibitors of these kinases or are to be used for screening for such activity; and to products such as arrays, microarrays and the like, that may be used to ascertain protein kinases that bind to and/or are inhibited by, the compounds.

By "inhibitors" is meant compounds that, e.g., bind to, partially or totally block stimulation, decrease, prevent, or delay activation, or inactivate, desensitize, or down-regulate signal transduction. Similarly, the term "inhibition" means a partial or total blocking, stimulation, decrease, prevention or delaying of activation, or inactivation, desensitizing or down-regulation of signal transduction.

DETAILED DESCRIPTION OF THE INVENTION

Figure 1:
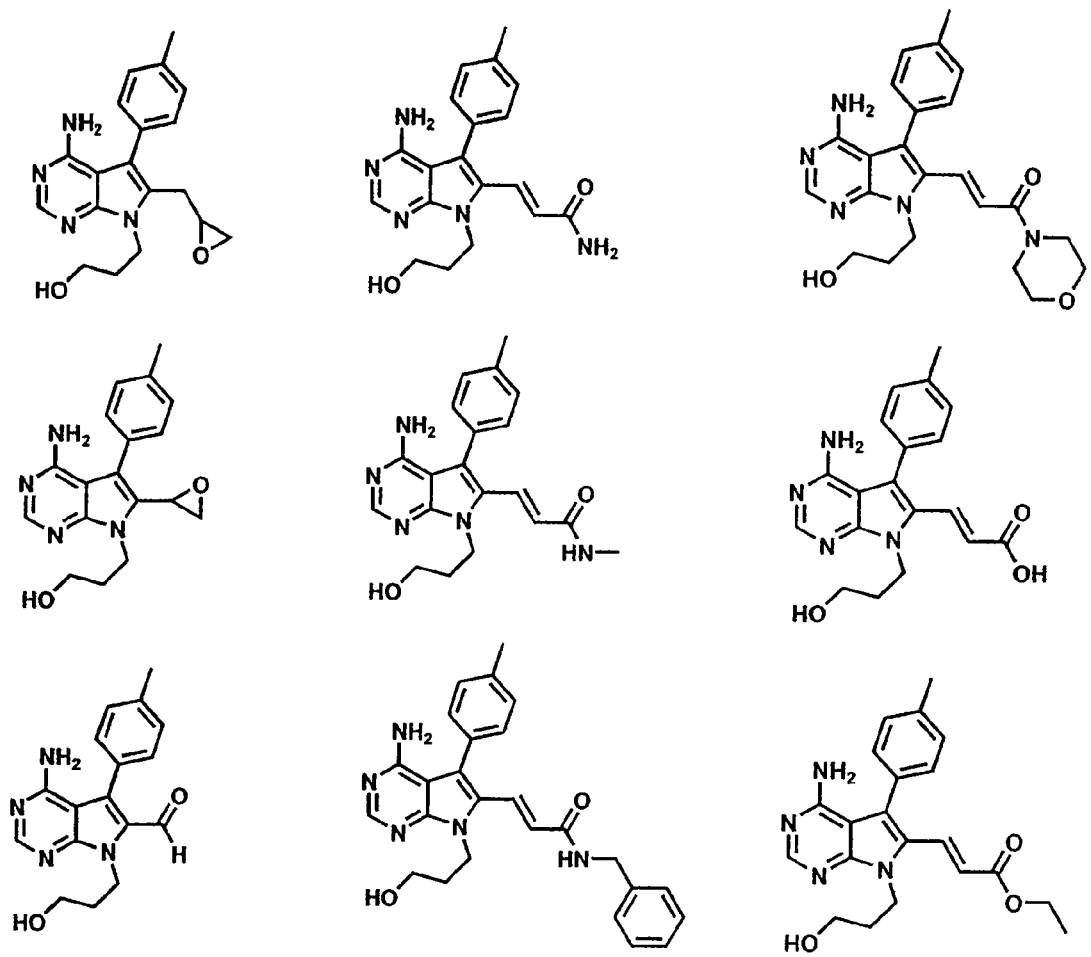
FIG. 1 depicts some representative compounds of the invention, in addition to those described herein.

This invention describes cell-permeable inhibitors that exploit a feature unique to the ATP-binding sites of three closely related kinases (Rsk1, Rsk 2, and Rsk 4; 80-90% sequence identity) and that also is present in certain other kinases. More specifically, Rsk 1,2,4 are unique among kinases in having a cysteine at the $CO_2H$-terminal end of the glycine-rich loop (corresponding to Cys436 of Rsk2) and a threonine in the gatekeeper position (corresponding to Thr493 of Rsk2) of their ATP-binding sites. These constitute specific recognition elements for the inhibitors described in this invention. As described below, certain compounds of this invention inhibit activity of these three kinases by forming a covalent bond with the cysteine and by interacting with the threonine in the gatekeeper position. In other instances, as described below, the compounds inhibit kinase activity by binding to a cysteine, while binding of the compound to a threonine or other residue might or might not take place.

The invention also describes a method for identifying inhibitors for eight other human protein kinases (Rsk3, Msk1, 2, Plk1-3, MEKK1, and Nek2), based on the presence of a key cysteine residue in their ATP-binding sites analogous to the cysteine found in Rsk1,2,4. At least two of these kinases, Plk1 and Nek2, are candidate anti-cancer targets based on their essential mitotic functions in model organisms.

Thus, compounds of this invention have a heterocyclic core structure comprised of two or more fused rings containing at least one nitrogen ring atom, and an electrophilic substituent that is capable of forming a covalent bond with a cysteine residue within the ATP binding site of the kinase. Optionally they may contain a second group that is capable of interacting with a threonine or smaller residue that is located in the gatekeeper position. Such a second group is necessary in compounds to be used for inhibition of Rsk1,2,4 but is optional in compounds to be used for inhibition of the other eight kinases discussed herein (Rsk3, Msk1,2, Plk1-3, MEKK1, and Nek2

The Rsk serine/threonine protein kinases are thought to have critical functions in the Ras/MAP kinase signaling pathway, a pathway which is deregulated in many human cancers. Of the four Rsk isoforms (Rsk1-4), Rsk1 and Rsk2 are the best characterized. Rsk1,2 are directly activated by the MAP kinases ERK1 and ERK2. Known substrates of Rsk1,2 include transcription factors involved in cell growth and differentiation (e.g. CREB, c-fos, estrogen receptor) and apoptosis (NF-κB). Rsk1,2 have thus been implicated in transcriptional control downstream of Ras and ERK1,2.

Rsk1-4 are unusual protein kinases in that they have two kinase domains, the NTD ($NH_2$-terminal domain) and the CTD ($CO_2H$-terminal domain). All Rsk substrates characterized thus far are phosphorylated by the NTD. Downstream signaling by the NTD requires at least three sequential phosphorylation events: (1) phosphorylation of the CTD activation loop (T573) by ERK1,2; (2) intramolecular phosphorylation of a linker region (S380) by the CTD, which creates a docking site for the kinase, PDK1; (3) phosphorylation of the NTD activation loop (S221) by PDK1. This invention describes inhibitors that specifically target the Rsk CTD, which therefore indirectly inhibit downstream signaling by the NTD.

In one aspect, this invention relates to certain novel compounds that inhibit one or more of the protein kinases referred to herein, the compounds having a heterocyclic core structure comprised of two or more fused rings containing at least one nitrogen ring atom, and an electrophilic substituent that is capable of forming a covalent bond with a cysteine in the ATP binding site of Rsk1-4, Msk1-2, Plk1-3, MEKK1, and Nek2, as shown in Sequence I below. The covalent bond is usually formed between the electrophilic substituent and the sulfhydryl group of the cysteine and may be a reversible or irreversible bond. Most preferably, the covalent bond is irreversible.

In another aspect this invention relates to a method of inhibiting (preferably inhibiting by formation of a covalent bond that is either reversible or irreversible, and most preferably irreversible) a protein kinase that has one or more cysteine residues within its ATP binding site, and more particularly a cysteine corresponding to the cysteine found in Rsk2, Nek2, MEKK1, Msk1, and Plk1 (see Sequence I below) comprising contacting the kinase with an inhibitory-effective amount of a compound as described herein.

In yet another aspect this invention relates to a method for inhibiting the morphological transformation of a cell in which such a kinase is expressed by contacting the cell or the kinase with an inhibitory-effective amount of a compound as described herein. For instance, contacting cells with a compound of the invention may inhibit the transformation of cells from a round to a flat morphology.

In yet another aspect this invention relates to a method for inhibiting proliferation of tumor cells or for inducing apoptosis in such cells, particularly melanoma or leukemia cells, by contacting such cells with an effective kinase-inhibiting amount of a compound of this invention.

Contacting cells with an inhibitory-effective amount of compounds of this invention may be done in any manner suitable for the particular method employed, and may be done in vitro or in vivo. In vitro methods include bringing the compound or compounds in question into contact with an isolated kinase or a collection of kinases, or with cells containing the kinase, in appropriate laboratory, analytical, or diagnostic devices or equipment. In vivo methods include administering an inhibitory effective amount of a compound or compounds, or of a formulation or composition containing the same, to a patient or subject in such a manner that the compound or compounds are delivered to a location in which the inhibition is desired. Various methods of administration may be used, for example, topical administration or systemic administration. In the latter case the compounds may be administered using any of a number of drug delivery techniques aimed at delivering the active compound to the location where inhibition is desired.

In other aspects the invention relates to methods for screening candidate compounds for activity as inhibitors of the kinases or for various therapeutic or pharmaceutical properties or activities to which inhibition of a kinase activity may be relevant, for example for pre-screening or screening compounds for anti-cancer or other activity, to libraries such as combinatorial libraries containing compounds that either have been found to be inhibitors of these kinases or are to be used for screening for such activity, and to products such as arrays, microarrays and the like, that may be used to ascertain proteins that bind to and/or are inhibited by, the compounds.

The compounds that form one aspect of this invention are compounds that have a heterocyclic core, preferably a core composed of two or more fused rings (most preferably from 2-5 fused rings) containing at least one nitrogen ring atom, and that have an electrophilic ring substituent. One preferred type of such compounds is the pyrrolopyrimidines. In addition to the one or more nitrogen atoms the compounds may also have one or more other heterocyclic ring atoms such as oxygen or sulfur.

More particularly, the compounds that are effective as inhibitors of the kinases include those having the formulas (I) or (IA) or formulas (II-V) shown below. Compounds of formulas (I) and (IA) are considered to be optimal for inhibiting Rsk-1,2,4 while compounds of formulas (II)-(V) are considered optimal for inhibiting Rsk3, Msk1,2, Plk1-3, MEKK1, and Nek2, which contain a cysteine homologous to Cys 436 of Rsk2.

One type of compound of the invention, shown below in Formulas (I) and (IA), is a pyrrolopyrimidine having an electrophilic substituent that may in general be located at any convenient position on the ring [Formula (I)] or preferably is at the C-6 position [Formula (IA)].

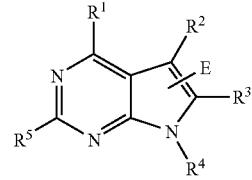

(I)

In Formula (I), $R^1$ is $NHR^a$ wherein $R^a$ is hydrogen or an optionally substituted aliphatic, aromatic or heterocyclic group (as defined herein) or $R^a$ is an electrophilic group E. $R^2$ is hydrogen or a group having the formula $(CH_2)_b R^b$ wherein b is 0 or an integer from 1 to 3 and $R^b$ is an aromatic, heterocyclic or cyclical aliphatic group optionally substituted with one or more groups selected from lower alkyl, halogen, substituted alkyl, nitro, alkoxy, phenoxy, sulfonamido, carboxylic ester, or carboxamide, or $R^2$ is an electrophilic group E as defined below. One preferred group for $R^2$ is p-tolyl, $-C_6H_4CH_3$, where the methyl group is situated in the para position on the phenyl ring with respect to the pyrrolopyrimidine moiety. $R^3$ is hydrogen or an aliphatic, aromatic, or heterocyclic group or an electrophilic group E as defined below. $R^4$ is an aliphatic, aromatic, or heterocyclic group optionally substituted with one or more polar groups such as hydroxyl, sulfhydryl or amino (which term includes substituted amino such as alkylamino, etc.), which polar group may be protected or unprotected, or an electrophilic group E as defined below. $R^5$ is usually hydrogen but can be an alkyl- or aryl-substituted ether, thioether, or amine, or an electrophilic group E as defined below. However, one of $R^1$-$R^5$ is an electrophilic group E. By the term "one of $R^1$-$R^5$ is an electrophilic group E" is meant that one of groups $R^1$-$R^5$ must be a group E, but only one of said groups may be E.

The electrophilic group E is most preferably one that comprises a carbonyl, an epoxide, or an olefin conjugated to an electron withdrawing group such as a carbonyl, nitro, cyano, carboxyl, carboxamide, sulfoxide, sulfonyl, sulfonamide, or sulfonate. For carbonyl groups, ketonic groups $-(CH_2)_m COR'$ and $-CO(CH_2)_n R'$ are preferred (m and n independently are 0 or an integer from 1 to 6 and R' is hydrogen, halogen, amino, substituted amino, cyano, or an optionally substituted aliphatic, aromatic or heterocyclic group). Alternatively the ketone may be a diketone $-C(O)C(O)R'$ where R' is as defined above. Groups that form "haloketones", such as $-C(O)Cl$, $-C(O)F$, $-CH_2C(O)Cl$, $-CH_2C(O)F$ (acyl halides), $-C(O)CH_2Cl$, $-C(O)CH_2Br$, $-C(O)CH_2F$, $-C(O)CHF_2$, $-C(O)CF_3$, etc. (halomethyl ketones), $-C(O)CH_2CN$ (cyanomethylketone), diketones, α-heterocyclic substituted ketones (—C(O)R', where R' is a heterocyclic group), and groups that form olefinically unsaturated ketones, such as —C(O)CH=CH$_2$ or —CH=CH—C(O)CH$_3$, are preferred. Olefin carboxylates have the general formula —CH=CHC(O)OR$_c$ where R$_c$ is an optionally substituted aliphatic, aromatic, or heterocyclic moiety. Olefin carboxamides have the general formula —CH=C(O)NR"R'" where R" and R'" are optionally substituted aliphatic, aromatic, or heterocyclic moieties. Epoxides contain from 2 to 4 carbon atoms and include, for example, epoxyethyl, epoxypropyl, and the like. Representative compounds and electrophilic groups of the invention are exemplified in the specification and in FIG. 1.

As used herein, "aliphatic" means a straight or branched chain acyclic, or non-aromatic cyclical, hydrocarbon radical, or combination thereof, which may be fully saturated, or mono- or polyunsaturated having the number of carbon atoms designated (i.e. $C_1$-$C_{10}$ means one to ten carbon atoms). Examples of saturated acyclic aliphatic groups (also termed alkyl groups) include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated aliphatic group is one having one or more double bonds or triple bonds. Examples of unsaturated acyclic aliphatic groups include alkenyl and alkynyl groups such as vinyl, 2-propenyl, isopropenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Examples of cyclical aliphatic groups include cyclopropyl, cyclobutyl, cyclopentyl, cyclohexyl, cyclopentenyl, cyclohexenyl, cyclohexadienyl, and the like. The terms "lower alkyl", "lower alkenyl" and "lower alkynyl" mean a group of the type mentioned, having up to six carbon atoms. For use in the invention, aliphatic groups generally may be of any desirable size. Preferably they will contain up to 20, most preferably, up to 10, carbon atoms. The aliphatic groups used in this invention may be unsubstituted or may be mono- or polysubstituted.

"Aromatic" or "aryl" refers to the typical substituted or unsubstituted non-aliphatic hydrocarbyl groups of this class, i.e., a polyunsaturated, typically aromatic, hydrocarbon substituent, which can be a single ring or multiple rings (up to three rings) which are fused together or linked covalently, such as phenyl, naphthyl, and the like. This class of moieties also includes fused-ring moieties such as indanyl, etc.

"Heterocyclic" refers to saturated or unsaturated cyclical moieties containing carbon atoms in the ring and additionally one or more hetero atoms, which are typically oxygen, nitrogen, sulfur and or phosphorus, such as pyridinyl, piperidinyl, pyrrolidinyl, morpholinyl, pyranyl, thienyl, furyl, thiazolyl, and fused-ring moieties such as benzoxazolyl, benzthiazolyl, etc. These may be optionally substituted with one or more substituents such as halogen, hydroxy, optionally substituted lower alkyl and optionally substituted lower alkoxy. Heterocyclic groups include heteroaromatic groups, and heteroaliphatic groups. Heteroaromatic groups are analogous to aromatic groups and include, for example, pyridyl, pyrimidinyl, pyrazolyl, pyrazinyl, thiazinyl, thienyl, furyl, imidazolyl, pyrrolyl, benzoxazolyl, benzthiazolyl, quinolyl, etc. Heteroaliphatic groups are saturated or partially unsaturated, and include, for example, pyrrolidinyl, morpholinyl, pyranyl, etc.

Aliphatic, aromatic and heterocyclic groups in compounds of this invention may be unsubstituted or may have one or more substituents, providing that such substituents do not interfere with the kinase-binding properties of the compounds. Substituents may include, for example, halo, hydroxyl, sulfhydryl, nitro, amino, substituted amino, amide, substituted amide, alkoxy, haloalkoxy, alkylenedioxy, alkyl, haloalkyl, hydroxyalkyl, sulfonyl, and the like.

Substituted aliphatic groups also include arylalkyl groups, namely alkyl groups subsisted by one or more aryl groups; for instance, benzyl, phenethyl, triphenylmethyl, and the like. The aromatic ring or rings in the arylalkyl groups may be further substituted similarly to other aromatic groups, e.g. chlorobenzyl, methylbenzyl, etc. Substituted aliphatic groups also include alkyl groups substituted by one or more saturated or unsaturated heterocyclic groups, e.g., pyridylmethyl, pyridylethyl, piperidinylmethyl, pyrrolidinylmethyl, morpholinylmethyl, quinolylmethyl, etc or by one or more optionally substituted cycloaliphatic groups such as cyclopropylmethyl or cyclohexylmethyl. Such groups may be substituted similarly to other heterocyclic or cyclic aliphatic groups, for example by one or more halogens, hydroxyl groups, lower alkyl groups, or lower alkoxy groups (including combinations of such groups).

"Protecting group" refers to any of a large number of groups used to replace one or both hydrogens of a reactive group such as a hydroxy, amino or sulfhydryl group, so as to block, prevent, or reduce reactivity of the group. Examples of protecting groups (and a listing of commonly used abbreviations for them) can be found in T. W. Greene and P. G. Futs, "Protective Groups in Organic Chemistry" (Wiley), Beaucage and Iyer, Tetrahedron 48:2223 (1992) and Harrison et al., Compendium of Synthetic Organic Methods, vols. 1-8 (Wiley).

Representative amino protecting groups include those that form a carbamate or amide with the nitrogen atom, as well as those groups collectively referred to in the Greene and Futs text as "special —NH protective groups". Representative examples of amino protecting groups include acetyl (Ac), trifluoroacetyl, benzyloxycarbonyl (Cbz), tert.-butoxycarbonyl (Boc), allyloxycarbonyl (Aoc), 9-fluorenylmethyloxycarbonyl (Fmoc), nitro-versatryloxycarbonyl (Nvoc), optionally substituted phthaloyl and the like.

Representative hydroxy protecting groups include those where the hydroxy group is either acylated or alkylated, such as by the formation of ethers or esters using, for instance, acetyl, benzyl, trityl, alkyl, tetrahydropyranyl, allyl and trisubstituted silyl groups.

The choice of a protecting group for a given compound, purpose or set of conditions is within the skill of those in the art, and is done so as to protect, generally or selectively, the reactive group in question under the prevailing conditions (presence of other reactive compounds, pH, temperature, etc.) Protecting groups that may be used in this invention and are mentioned herein include phthaloyl, acetyl (Ac), benzyl (Bn), 2,2,2-trichloroethoxycarbonyl (Troc), t-butyldimethylsilyl (TBS), t-butyldiphenylsilyl (TBDPS), and 2,2,2-trichloro-1,1-dimethylethyl chloroformyl (TCBOC) groups.

As is known in the art, a certain protecting group or type of group may be more suitable than others for use with a particular compound or in a given situation, and advantage is taken of these suitabilities in developing processes that involve compounds with reactive groups such as hydroxy and/or amino. Thus, a reaction scheme can be developed for producing or reacting certain compounds in which general or selective protection or deprotection (removal of protecting groups) is carried out at certain points. For instance, in order to selectively react a hydroxy group in a compound that also contains an amino group, or vice versa, the group whose reaction is not desired at this point can be blocked with a protecting group that is not removed under conditions of the reaction (for example, is not base-hydrolyzable if the reaction is to be conducted under basic conditions, while the group to be reacted can be protected by a group that is base-hydrolyzable, so that said group becomes unblocked, and thus reactive, at that time. Similarly, in order to selectively react a group, e.g., a hydroxyl group, located at one position in the molecule, it may be protected with a different protecting group than other hydroxyls in the molecule. As used herein, the designation "PG" refers to protecting groups that form esters, ethers or carbonates with hydroxy groups (i.e., with the oxygen atom of a hydroxy group] or that form amides or carbamates with amino groups [i.e. with the nitrogen atom of an amino group. The designation "PG'" is used herein to refer to optionally substituted phthaloyl groups, for example phthaloyl or tetrachlorophthaloyl, and which may be used to protect an amino group, as shown. However, in any event, the selection of particular protecting groups used or illustrated in the processes described herein is not in any way intended to limit the invention.

Formula (I) depicts compounds in which the electrophilic group E may be located at any position on the fused rings that is not otherwise occupied by a functional group (that is, a group other than hydrogen). However, in a preferred embodiment of this type of compound, the electrophilic group E is located at the C-6 position on the ring, i.e. in the place of group $R^3$ of formula (I). Such compounds preferably have the formula (IA) where $R^2$, $R^4$, $R^5$ and E are as defined above:

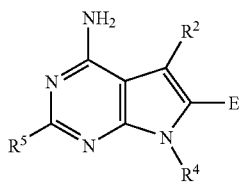

(IA)

and where preferred embodiments of $R^2$, $R^4$, $R^5$ and E are as described above with respect to Formula (I).

Another preferred type of compound of Formula (I) or Formula (IA) is one in which $R^4$ is an amino or substituted amino group and E is a halomethyl ketone (most preferably a fluoromethylketone) or an enone. Substituted amino groups for $R^4$ in such compounds include optionally substituted aliphatic and phenyl groups. Preferred aliphatic groups include optionally substituted lower alkyl, lower alkenyl and lower alkynyl groups, for example, propargyl, CH≡C—CH$_2$—. Representative compounds of this preferred type are

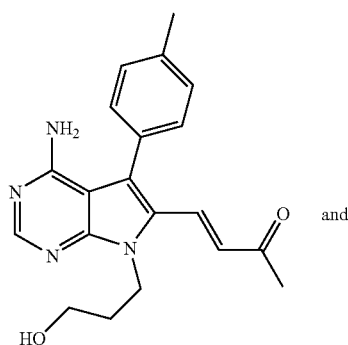

and

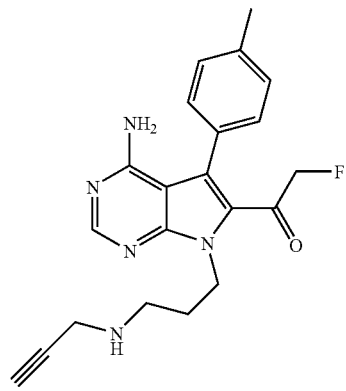

One such compound according to formula (IA) is known— in which E is cyano, $R^2$ is 4-phenoxyphenyl, $R^4$ is cyclopentyl and $R^5$ is hydrogen. This compound is mentioned by Burchat et al., Bioorg. & Med. Chem. Lett. 10:2171 (2000) as being an inhibitor of lck; however no information is given regarding inhibition of the kinases discussed herein.

The pyrrolopyrimidine compounds of the invention as shown in formulas (I) and (IA) can also be viewed as in Formula (IB) below, which illustrates functions for the purpose of this invention, of certain aspects of the structures of the pyrrolopyrimidines.

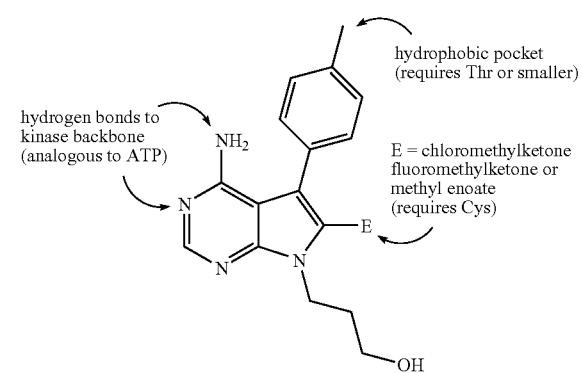

(IB)

Rsk inhibitors based on a pyrrolopyrimidine scaffold.

The invention also includes compounds having other structures containing electrophilic groups that also may be used for inhibition of these kinases and are optimal for Rsk3, Msk1,2, Plk1-3, MEKK1, and Nek2. Such compounds include, for instance, those having core structures shown below as formulas (II), (III), (IV) and (V):

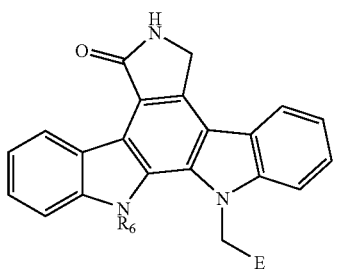

(II)

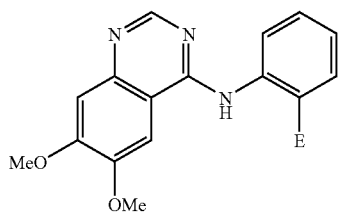

(III)

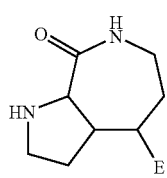

(IV)

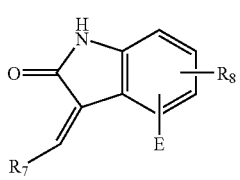

(V)

In formulas (II)-(V), E represents an electrophilic moiety as described herein. Preferably, for optimum inhibitory effect this group is located on the core heterocyclic ring in the positions shown. However, in compounds of this invention electrophilic group E may be located at other positions on the respective rings, similar to Formula (I) for pyrrolopyrimidines. Groups $R^6$ and $R^7$ may be hydrogen or optionally substituted aliphatic, aromatic or heterocyclic groups as defined above. In formula V, for example, group $R^7$ is preferably a group having the formula $(CH_2)_bR^b$ wherein b is 0 or an integer from 1 to 3 and $R^b$ is an aromatic, heterocyclic or cyclical aliphatic group. The group $R^7$ may be directly linked to the olefinic carbon or may be linked via an amino moiety. Compounds of Formula (III) may have substituents of the type $-O(CH_2)_pNR^d{}_2$, where p is an integer from 1 to 3 and $R^d$ is an alkyl group or the two $R^d$ groups may be combined with the nitrogen atom to form a nitrogen-containing heterocycle such as piperazine, piperidine or morpholine.

Some compounds of formula (V) include

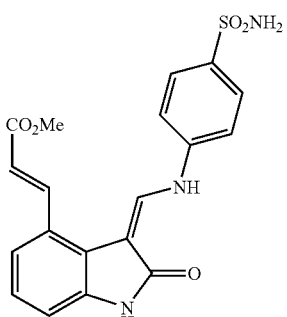

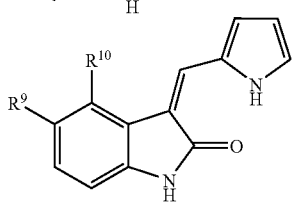

$R^9 = COCH_2Cl, R^{10} = H$ $R^9 = CHCH_2CO_2Me, R^{10} = H$ $R^9 = H, R^{10} = CHCH_2CO_2Me$

In addition to the substituents shown in the above core structures of formulas (II)-(V), the rings may be further substituted with other moieties, for example those indicated by the symbol $R_8$ in formula (V), so long as they do not affect the kinase-inhibiting properties of these compounds. In any case, the compounds specifically shown in formulas (II)-(V) possess the necessary kinase inhibiting capabilities.

Figure 5:
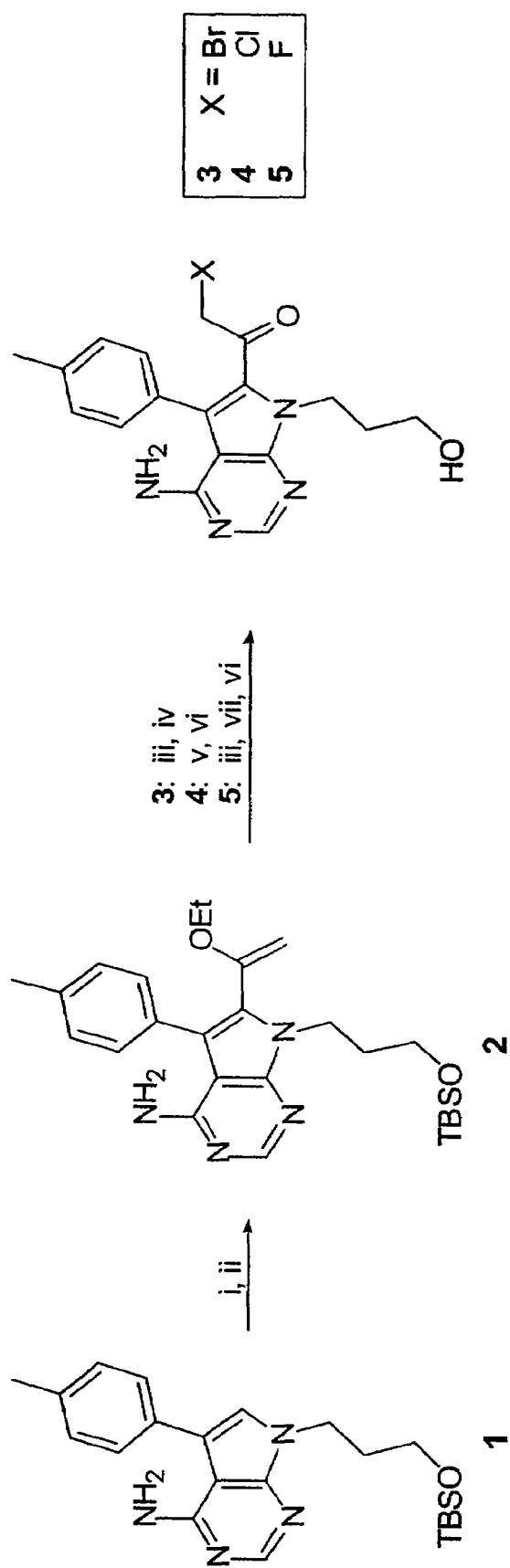
FIG. 5 depicts the synthesis route for halomethyl ketones.

Compounds of formulas (I) and (IA) are synthesized by methods, for example, as shown in FIG. 5 and Scheme A, below, through a scaffold compound or intermediate having the corresponding formula but lacking the electrophilic group E.

For compounds (IA) such an intermediate has the general formula (IC):

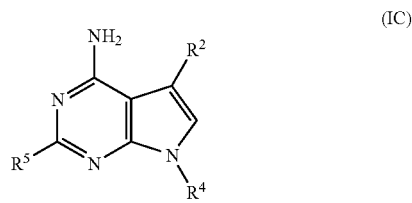

(IC)

where $R^2$, $R^4$ and $R^5$ are as defined above.

Chemical synthesis of halomethyl ketone derivatives is described in FIG. 5. First, 1 was synthesized in overall 48% yield from commercially available materials. The hydroxypropyl substituent at N7 was chosen so that an affinity tag (e.g. biotin) could be attached to this position.

Halomethylketones 3-5 were synthesized as illustrated in FIG. 5. Referring to that Figure, the synthesis commences with the selective bromination of the 6-position of 1 with NBS (80% yield). Conversion of 6-bromo 1 to enol ether 2 was accomplished in 82% yield by palladium catalyzed Stille coupling with α-(ethoxy vinyl)tributyl tin. Enol ether 2 served as a key intermediate from which compounds 3-5 could be synthesized in two or three steps. Bromomethylketone (bmk) 3 was synthesized in 60% yield via bromination of 2 with NBS at −20° C., followed by removal of the TBS protecting group with 1N HBr. Because of the electron donating effects of the nitrogen in the pyrrole ring of 2, chloromethylketone (cmk) 4 could be synthesized directly from 2 with the less reactive electrophilic halogenating reagent, NCS, albeit in modest yield (40% overall), following TBS removal with 1N HCl. Nucleophilic fluorination of 3 with KF and subsequent TBS removal furnished fluoromethylketone (fmk) 5 in 42% overall yield.

Compounds of formula (II) may be prepared in general by adapting procedures from Kuo et al. (*J. Med. Chem.* (2003), 46: 4021-4031), and references found therein.

Compounds of formula (III) may be prepared in general by adapting procedures from Bridges et al. [*J. Med. Chem.* (1996), 39: 267-276], and references found therein.

Compounds of formula (IV) may be prepared in general by adapting procedures from Wan et al. (*Chem. Biol.* (2004), 11: 247-259), and references found therein.

Compounds of formula (V) may be prepared by reaction of the appropriate iodooxindole with an alkylating agent so as to add the desired group $R^7$, followed by reaction in the presence of a palladium catalyst to add the electrophilic group, as shown in some of the examples below. Alternatively an oxindole containing the electrophilic group may first be prepared, followed by addition of the group $R^7$, also as shown in preparation examples below.

Compounds that inhibit the kinases according to this invention would be useful as anti-cancer and/or anti-inflammatory drugs and/or as immunosuppressants. In addition they also would be useful as inhibitors to probe the function of specific serine/threonine kinases in mammalian cells.

Formulation and Administration.

Compounds identified as active kinase inhibitors can be administered to a patient or subject at doses effective to inhibit kinases or at therapeutically effective doses to prevent, treat, or control conditions, for example to act as immunosuppressive or anti-inflammatory agents. Compositions containing the substances are administered to a patient or subject in an amount sufficient to elicit an effective therapeutic response in the patient. An amount adequate to accomplish this is defined as a "therapeutically effective dose" or "therapeutically effective amount". The dose or amount will be determined by the efficacy of the particular active substance employed and the condition of the subject. The size of the dose also will be determined by the existence, nature, and extent of any adverse effects that accompany the administration of a particular compound in a particular subject. Typically, the patient or subject is human. However, the patient or subject may be a non-human mammal (e.g., a primate, a mouse, a pig, a cow, a cat, a goat, a rabbit, a rat, a guinea pig, a hamster, a horse, a sheep, a dog, a cat and the like), and may be male or female.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and thereby reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, sublingually, intranasally, orally, parenterally (e.g., intravenously, intraperitoneally, intramuscularly, subcutaneously, intravesically or intrathecally), or mucosally (including intranasally, orally and rectally).

For oral or sublingual administration, pharmaceutical compositions of compositions of the invention can take the form of, for example, lozenges, tablets or capsules prepared by conventional means with pharmaceutically acceptable excipients, including binding agents, for example, pregelatinized cornstarch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulfate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compositions of the invention may also be formulated in rectal compositions such as suppositories or retention enemas, e.g., containing conventional suppository bases such as cocoa butter or other glycerides.

The compositions of the invention may also be formulated for transdermal administration. For transdermal administration, the active compounds are formulated into ointments, salves, gels, or creams as generally known in the art. Pharmaceutical compositions adapted for transdermal administration can be provided as discrete patches intended to remain in intimate contact with the epidermis for a prolonged period of time. If the compositions of the invention are to be administered topically, the compositions can be formulated in the form of, e.g., an ointment, cream, transdermal patch, lotion, gel, spray, aerosol, solution, emulsion, or other form well-known to one of skill in the art. For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as Freon), or in a squeeze bottle. Moisturizers or humectants can also be added to pharmaceutical compositions and dosage forms if desired. Examples of such additional ingredients are well-known in the art. Compositions may also be included in a device for transdermal delivery such as a skin patch or a more complex device.

The compounds also may be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions may also be in the form of controlled release or sustained release compositions as known in the art, for instance, in matrices of biodegradable or non-biodegradable injectable polymeric microspheres or microcapsules, in liposomes, in emulsions, and the like.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Depending on their chemical and physical nature, kinase-inhibitory compounds may be included in the compositions and administered to the patient per se, or in another form such as a salt, solvate, complex, chelate or other derivative as appropriate or as needed for good formulation or administration of the substance. Likewise, a prodrug of the substance may be included in the compositions, that is, a substance that releases the active substance either on preparation of the composition or on administration of the composition to the patient or subject.

In carrying out the invention, a single inhibitory compound, or a combination of compounds according to this invention, i.e. that interact with and produce inhibition of, relevant kinases, may be administered to a patient. The effective compounds may be administered alone or in combination with (or in time proximity to) other therapeutic agents administered for similar or other therapeutic purposes, for example administration of a compound according to this invention together with an adjuvant or other anti-inflammatory agent. Similarly, compositions containing one or more of the compounds of this invention may also contain other pharmaceutical or therapeutic agents.

The present invention also includes arrays for testing substances for interaction with or binding to the kinases. Typically such arrays will be used for testing combinatorial or other libraries. The arrays will comprise standard equipment such as a plate, which will contain kinases arranged on the surface of the plate, for example in wells or bound to certain locations on the surface. A plate or array may contain kinases of a single type or it may contain different kinases, located in prearranged fashion.

In one aspect the invention provides in vitro, ex vivo, and in vivo assays for inhibitors of the eleven kinases described herein, either as a group or individually. In particular, the assays can be used to test for compounds that possess this activity for testing for binding to or inhibition of the activity of the kinase or kinases in question. Typically in such assays, the compound or compounds to be tested are contacted with the kinase or kinases and suitable tests are carried out to ascertain whether the normal activity of the kinase(s) has been inhibited. For example, the results of the assay may be compared to a control assay that comprises the kinase(s) alone, without the test compound(s), using any known activity of the kinase(s) as the comparison standard.

Methods for prescreening for an agent that inhibits a kinase of the type described herein, may comprise contacting such a kinase or a cell containing or expressing it with a compound of the invention and detecting specific binding of the compound to the kinase. The detecting may be carried out via a method such as capillary electrophoresis, Western blot, mass spectroscopy, ELISA, immunochromatography, or immunohistochemistry. In one embodiment, the compound can be contacted directly to the kinase. In another embodiment, the test agent is contacted to a cell containing the kinase.

Binding of test compounds to kinases can be performed in solution, in a bilayer membrane, attached to a solid phase, in a lipid monolayer, or in vesicles. Binding of test compounds to the kinases can be tested by measuring or observing changes in kinase activity or by, e.g., changes in spectroscopic characteristics or in chromatographic or solubility properties. Binding of test compounds can also be ascertained in competitive binding assays, for example, by ascertaining whether unlabeled test compounds prevent the interaction between the kinase and a biotinylated or fluorescent derivative of a reference compound.

The assays that form an aspect of this invention may be designed to screen large chemical libraries for inhibition of one or more of the kinases using automated assay steps, which are typically run in parallel (e.g., in microtiter formats on microtiter plates in robotic assays). In one preferred embodiment, high throughput screening methods are used that involve providing a combinatorial chemical or other library containing a large number of potential inhibitory compounds. Such libraries are then screened in one or more assays, as described herein, to identify those library members (either particular chemical species or subclasses) that display the desired activity. When screening for modulators, a positive assay result need not indicate that particular test agent is a good pharmaceutical. Rather, a positive test result can simply indicate that the test agent can be used to inhibit activity of a kinase and/or can also serve as a lead compound in the development of other inhibitors. The compounds thus identified may serve as conventional "lead compounds" or may themselves be used as potential or actual therapeutics.

Thus, another aspect of this invention lies in libraries, such as combinatorial libraries, of compounds that are produced for testing based on activity, i.e., inhibition of one or more of the kinases described herein, within the general definitions of compounds herein, such as formulas (I)-(V). A combinatorial chemical library is a collection of such chemical compounds generated by either chemical synthesis or biological synthesis, by combining a number of chemical "building blocks" such as reagents. For example, a linear combinatorial chemical library is formed by combining a set of chemical building blocks in every possible way for a given compound type. Millions of chemical compounds can be synthesized through such combinatorial mixing of chemical building blocks.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

Other aspects of the invention involve the engineering or modification of protein kinases other than Rsk1-4, Msk1-2, Plk1-3, MEKK1, and Nek2 so as to render them susceptible to inhibition, for instance, by the compounds described herein. Thus, this invention also involves the engineering or modification of a protein kinase by replacing a valine residue within the ATP binding site of the protein kinase with a cysteine residue. This can render the enyzmatic activity of the modified protein kinase susceptible to inhibition by the compounds disclosed herein.

Alternatively, this invention involves the engineering or modification of a protein kinase that already contains a cysteine in the ATP-binding site corresponding to Cys436 of Rsk2. These kinases include Rsk3, Msk1-2, Plk1-3, MEKK1, and Nek2. The engineering or modification of the protein kinase is achieved by replacing a methionine, leucine, isoleucine, lysine, arginine, tryptophan, glutamine, asparagine, proline, tyrosine, histidine, glutamic acid, aspartic acid, valine, or phenylalanine residue in the gatekeeper position of the ATP binding site with a smaller residue, e.g. a threonine, serine, alanine, or glycine residue. This can render the kinase susceptible to inhibition by some compounds of this invention, and can serve to identify such compounds.

Selective inhibitors of individual kinases are useful as tools for elucidating kinase function in signaling networks; however, it is difficult to find such inhibitors due to the highly conserved nature of the kinase catalytic domain. However, engineering or modification of a protein kinase can transform a kinase that has no known inhibitors (or that can be only inhibited reversibly) into one that for the first time can be inhibited (or can be inhibited irreversibly), for example by compounds of this invention. The now modified kinase can be used to elucidate kinase functioning in signaling networks, for example by being introduces into genetically transformed animals.

Chemical genetic strategies have been successfully used to generate highly selective inhibitors for a single engineered kinase. The aspects of this invention that relate to engineering or modifying kinases involve a new chemical genetic approach that relies on the design of active site-directed, electrophilic tyrosine kinase inhibitors. The method involves replacing a conserved valine in the active site of selected Src tyrosine kinases with a nucleophilic cysteine residue. The compounds of this invention, containing electrophilic groups as described herein, were synthesized by appending halomethylketone substituents to the C6 position of a pyrrolo[2,3-d]pyrimidine scaffold. The inhibitors selectively and irreversibly inactivated the engineered kinases in vitro and in vivo.

According to the present invention, selective inhibition of individual kinases is achieved using a chemical genetic approach. This method involves engineering a suitably poised nucleophile in the ATP-binding site to react with an electrophilic inhibitor, thus promoting covalent inactivation of the kinase.

Electrophilic inhibitors, as in the compounds of this invention, are advantageous over reversible inhibitors for two reasons. First, because the dissociation rate is zero, the concentrations needed to block protein function are potentially much lower than reversible inhibitors. This is especially true for protein kinase inhibitors, which almost always bind competitively with respect to ATP (present in the cytoplasm at millimolar concentrations). Second, electrophilic inhibitors have an additional element of specificity that is dependent on covalent bond formation. For example, the acrylamide-substituted quinazoline, PD 168393, was shown to specifically alkylate a cysteine residue in the ATP-binding site of the epidermal growth factor receptor. PD 168393 was far superior to reversible quinazoline inhibitors in an animal carcinoma model.

Electrophilic pyrrolopyrimidines were synthesized that reacted with an engineered cysteine residue in the ATP-binding site of Src-family tyrosine kinases. The novel compounds of this invention potently inactivated the engineered kinases, yet were poor inhibitors of wild-type (wt) enzymes. Importantly, a chloromethylketone (cmk) derivative (4) irreversibly blocked the function of mutant v-Src in mammalian cells, yet had no effect on wt v-Src.

Recently, the crystal structure of Hck (a Src-family kinase) in complex with PP1 was determined. This structure shows PP1 bound within the ATP-binding site of the kinase, with the tolyl substituent inserted into an adjacent hydrophobic pocket. For the compounds of this invention, we selected valine 281 to mutate to cysteine. Val281 is adjacent to a flexible, glycine-rich loop. Thus we considered it to be more likely that a cysteine at this position would be properly oriented for nucleophilic attack. Compounds having an electrophile-bearing carbon in place of the N6 of PP1 were conceived and prepared.

Inhibitor Design

Rsk inhibitors were designed to occupy the ATP-binding pocket based on several key interactions with a pyrrolopyrimidine scaffold Using a structure-based sequence alignment (Sequence I below;), we found that Cys 436 in human Rsk2 would be suitably oriented to react with a pyrrolopyrimidine compound having an electrophilic moiety such as a chloromethylketone or a methyl enoate at the C6 position. This is the most crucial specificity element of the inhibitor, as only 111 of the 518 human kinases (Rsk1-4, Msk1,2, Plk1-3, MEKK1, and Nek2) have a cysteine in this position.

The following shows a structure-based sequence alignment of kinase domains with a cysteine that we predicted to interact with C6-substituted electrophilic pyrrolopyrimidines. The tyrosine kinase Src, which binds the known inhibitor PP1, is shown for reference. Cysteines, valines, methionines, leucines and threonines referred to herein are highlighted in bold italics.

```
src    -------LRLEVK-LGQGCFGEVWMGTWNG--TTRVAIKTLKPGTMS---
rsk2   -IQFTDGYEVKED-IGVGSYSVCKRCIHKATN-MEFAVKIIDKS------
nek2   MPSRVEDYEVLHS-IGTGSYGRCQKIRRKSDG-KILVWKELDYGSMT---
mekk1  --REDTEWLKGQQ-IGLGAFSSCYQAQDVGTG-TLMAVKQVTYVRNTSSE
msk1   ----HYDLDLKDKPLGEGSFSICRKCVHKKSN-QALQVKIISKR------
plk1   -----RRRYVRGRFLGKGGFAKCFEISDADTK-EVFAGKIVPKSLLLK--
src    ----PEAFLQEAQVMK--KLRHEKLVQLYAVVSEEP---IYIVTEYM
rsk2   ----KRDPTEEIEILLR-YGQHPNIITLKDVYDDGKY--VYVVTELM
nek2   -EVEKQMLVSEVNLLR--ELKHPNIVRYYDRIIDRTNTTLYIVMEYC
mekk1  QEEVVEALREEIRMMS--HLNHPNIIRMLGATCEKSN--YNLFIEWM
msk1   ---MEANTQKEITALK-LCEGHPNIVKLHEVFHDQLH--TFLVMELL
plk1   -PHQREKMSMEISIHR--SLAHQHVVGFHGFFEDNDF--VFVVLELC
```

We also determined that Thr 493 of Rsk2 could accommodate a large aromatic substituent at C5 of the pyrrolopyrimidine scaffold and could form a hydrogen bond with the exocyclic amine. With the exception of Rsk1,2,4, all of the aforementioned kinases have a large amino acid at this position (methionine, leucine, or isoleucine). Thus, Rsk1,2,4 are protein kinases that are irreversibly inhibited by the compound shown in Formula IA.

The invention is further illustrated by the following examples.

Preparation of Compounds of Formula IA

Electrophilic Rsk inhibitors 1 (formula IA, chloromethyl ketone) and 2 (formula IA, methyl enoate) were synthesized in eight and seven steps, respectively, starting from p-methyl-α-bromoacetophenone, as shown and described below (Scheme A). Inhibitors 3-5 (bromomethyl, chloromethyl and fluoromethyl ketones of Formula IA, respectively) were prepared as shown in FIG. 5. Biotin-1 was prepared by reacting 1 with biotin-aminocaproic acid in the presence of MSNT. All intermediates were characterized by mass spectrometry and $^1$H NMR.

Scheme A. Synthesis of Rsk inhibitors 1 and 2.

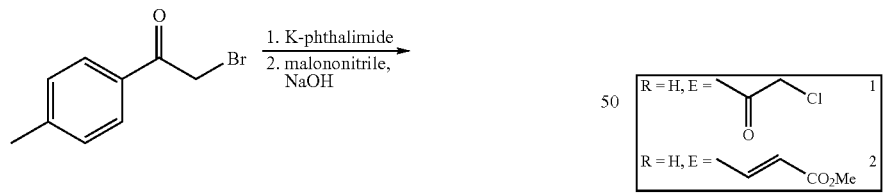

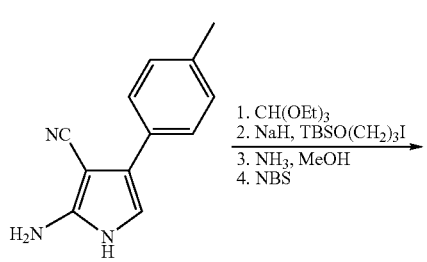

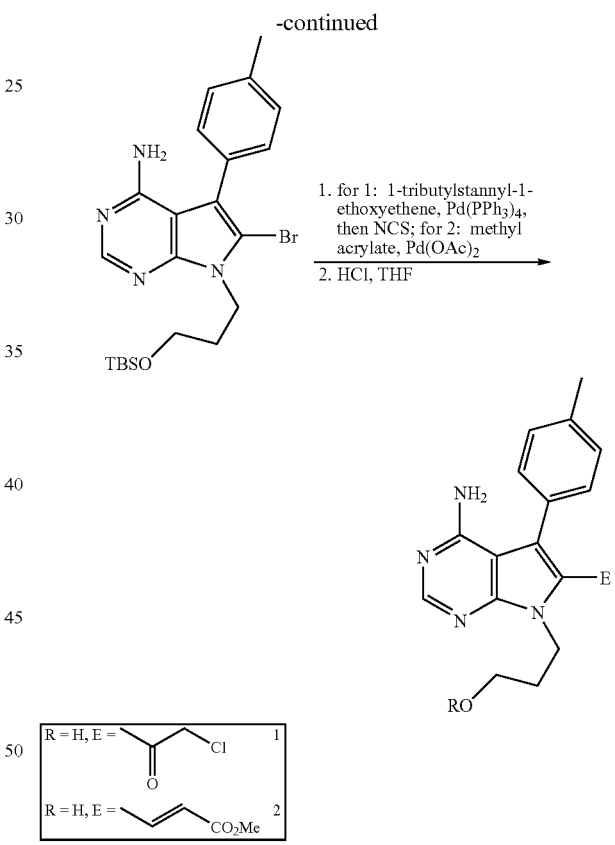

Materials.

All solvents were of ACS chemical grade (Fisher) and were used without further purification unless otherwise indicated. Methylene chloride was dried by distillation from calcium hydride. Tetrahydrofuran was distilled from sodium/benzophenone ketyl. All starting materials and synthetic reagents were purchased from commercial sources unless otherwise noted.

General Experimental.

$^1$H NMR and $^{13}$C NMR spectra were recorded on a Varian 400 spectrometer at 400 and 100 MHz, respectively. Low-resolution electrospray ionization mass spectra were recorded on a Waters ZQ 4000. High-resolution electron impact mass spectra were recorded on a MicoMass VG70E spectrometer. Analytical and preparative thin layer chromatography was preformed with EM Science silica gel 60 F$_{254}$ glass plates. Flash chromatography was conducted with Merck silica gel 60 (230-400 mesh).

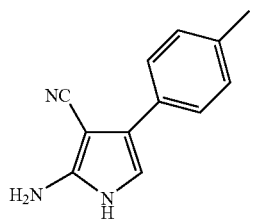

Step 1. To a solution of malononitrile (3.24 g, 48.9 mmol) in 6:1:1 MeOH/48% aq. NaOH/H$_2$O (56 mL) was added 2-phthalamido-4'-methylacetophenone[1] (10.5 g, 37.6 mmol). The reaction mixture was stirred at room temperature for 1 h upon which the product precipitated out of solution. The solid was collected by filtration, washed with H$_2$O, CH$_2$Cl$_2$, and hexanes to give 6.7 g (91% yield) of the pyrrole as a brown solid: R$_f$ 0.70 (10% MeOH/CH$_2$Cl$_2$); $^1$H NMR (400 MHz, CD$_3$OD) δ7.409 (d, J=7.6 Hz, 2H), 7.08 (d, J=7.6 Hz, 2H), 6.36 (s, 1H), 4.83 (br s 2H), 2.27 (s, 3H); $^{13}$C NMR (100 MHz, CD$_3$OD) (partial) δ136.9, 130.1, 126.6, 120.1, 109.0, 21.1.

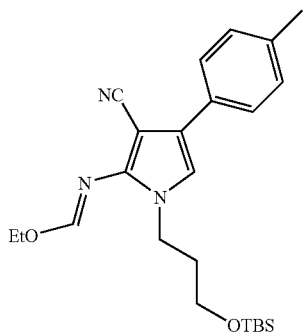

Step 2. A solution of the pyrrole (5 g, 25.3 mmol) in triethyl orthoformate (30 mL) was treated with acetic anhydride (0.5 mL) and refluxed for 1 h. After cooling to room temperature, the solvent was removed in vacuo. The crude pyrrole imino ether was azeotropically dried with toluene (2×10 mL) and carried on directly to the next step.

To a solution of NaH (60% in oil, 0.9 g, 23.4 mmol) in 20 mL of DMF at room temperature was added a solution of pyrrole imino ether in 10 mL of DMF. After stirring for 30 min, 3-(t-butyldimethylsilyloxy)propyl iodide[2] (7.0 g, 23.4 mmol) was added over 10 min. After stirring for an additional 3 h, the solvent was removed in vacuo and the residue was purified by flash chromatography (10-50% ethyl acetate/hexanes) to afford 5 g (70% yield) of the N-alkyl pyrrole imino ether as a brown oil: R$_f$ 0.8 (4:1 hexanes/ethyl acetate); $^1$H NMR (400 MHz, CDCl$_3$) δ8.43 (s, 1H), 7.47 (d, J=8.0 Hz, 2H), 7.16 (d, J=8.0 Hz, 2H), 6.62 (s, 1H), 4.32 (q, J=8.0 Hz, 2H), 3.96 (t, J=7.2 Hz, 2H), 3.59 (t, J=5.6 Hz, 2H), 2.33 (s, 3H), 1.91-1.82 (m, 2H), 1.37 (t, 3H), 0.88 (s, 9H), 0.03 (s, 6H); $^{13}$C NMR (100 MHz, CDCl$_3$) δ 158.2, 144.1, 136.8, 130.5, 129.7, 126.2, 125.0, 118.5, 115.6, 63.4, 59.7, 43.1, 33.4, 26.1, 21.4, 18.5, 14.2.

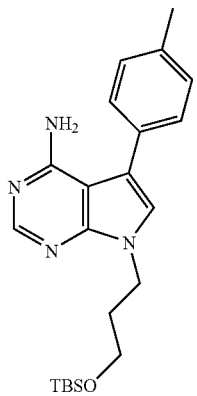

Pyrrolo[2,3-d]pyrimidine A.

The imino ether from step 2 (18.0 g, 42.3 mmol) was dissolved in MeOH (100 mL) and transferred to 350 mL sealed-tube reaction vessel. Argon gas was then bubbled through the solution for 15 min. Reaction vessel was submerged in a dry ice/MeOH bath and NH$_3$ gas was bubbled through the solution for 15 min to saturate. The reaction vessel was quickly sealed with a Teflon screw cap (fitted with a rubber O-ring) and allowed to warm to room temperature. The reaction was stirred for 4 days at 50° C. and then submerged in an ice bath and NH$_3$ gas was slowly released. The solvent was removed in vacuo and the crude product was purified by flash chromatography (3:2 ethyl acetate/hexanes with 1% Et$_3$N) to give 10.1 g (61% yield) of A as a light-brown solid: R$_f$ 0.41 (1:1 hexanes/ethyl acetate); $^1$H NMR (400 MHz, CDCl$_3$) δ 8.32 (s, 1H), 7.37 (d, J=8.4 Hz, 2H), 7.26 (d, J=8.0 Hz, 2H), 6.92 (s, 1H), 5.1 (br s, 2H), 4.34 (t, J=6.8 Hz, 2H), 3.65 (t, J=6.0 Hz, 2H), 2.41 (s, 3H), 2.10-2.05 (m, 2H), 0.91 (s, 9H), 0.05 (s, 6H); $^{13}$C NMR (100 MHz, CDCl$_3$) δ 156.9, 151.9, 150.6, 136.8, 132.0, 129.7, 128.7, 123.2, 115.8, 101.3, 59.8, 41.5, 33.0, 25.9, 21.1, 18.2; ESI-MS 419 [M+Na]$^+$, 397 [M+H]$^+$.

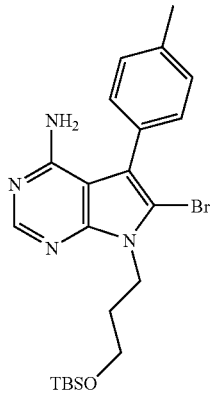

Bromide B.

To a solution of pyrrolo[2,3-d]pyrimidine A (1.5 g, 3.78 mmol) in DMF (20 mL) was added NBS (0.74 g, 4.16 mmol) and the mixture stirred for 24 h in the absence of light. The reaction was diluted with ether (100 mL) and washed with water (3×200 mL). The combined aqueous fractions were extracted with ether (3×50 mL). The combined organic fractions were dried over anhydrous Na$_2$SO$_4$, filtered, and concentrated in vacuo to give 1.77 g (99% yield) of bromide B as a brown solid: $R_f$ 0.59 (100% ethyl acetate); $^1$H NMR (400 MHz, CDCl$_3$) δ 8.21 (s, 1H), 7.35 (d, J=8.0 Hz, 2H), 7.30 (d, J=8.0 Hz, 2H), 5.0 (br s, 2H), 4.41 (t, J=6.8 Hz, 2H), 3.73 (t, J=6.0 Hz, 2H), 2.43 (s, 3H), 2.1 (m, 2H), 0.91 (s, 9H), 0.06 (s, 6H); ESI-MS 500 [M+2+Na]$^+$, 497 [M+Na]$^+$, 477 [M+2]$^+$, 475 [M]$^+$.

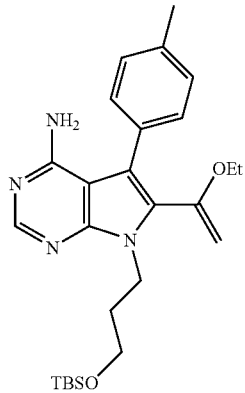

C

Enol Ether C.

To a solution of bromide B (389 mg, 0.82 mmol) in toluene (10 mL) was added α-(ethoxyvinyl)tin (0.390 mL, 1.15 mmol). Argon gas was bubbled through the solution for 10 min. Tetrakis(triphenylphosphine)palladium (95 mg, 0.082 mmol) was quickly added and mixture was refluxed for 16 h. The solvent was removed in vacuo and the crude product was purified by flash chromatography (50-100% hexanes/ethyl acetate) to give enol ether C (304 mg, 80% yield) as solid: $R_f$ 0.25 (1:1 hexanes/ethyl acetate); $^1$H NMR (400 MHz, CDCl$_3$) δ8.31 (s, 1H), 7.31 (d, J=8.0 Hz, 2H), 7.22 (d, J=8.0 Hz, 2H), 4.99 (br s, 2H), 4.39 (s, 1H), 4.37 (t, 2H), 4.17 (s, 1H), 3.84 (q, J=6.8 Hz, 2H), 3.72 (t, 2H), 2.40 (s, 3H), 2.1 (m, 2H), 1.34 (t, 3H), 0.89 (s, 9H), 0.05 (s, 6H); $^{13}$C NMR (100 MHz, CDCl$_3$) δ157.3, 152.4, 152.0, 150.2, 137.1, 131.9, 130.9, 130.2, 129.4, 114.9, 101.7, 91.6, 63.6, 61.2, 41.2, 33.5, 26.1, 21.4, 18.5, 14.6; ESI-MS 489 [M+Na]$^+$, 467 [M+H]$^+$.

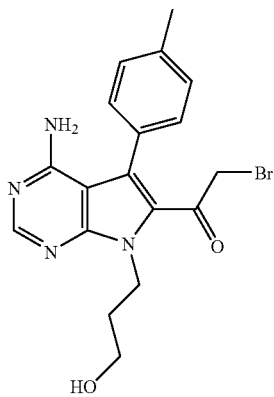

3

Bromomethyl Ketone (bmk) 3.

To a solution of enol ether C (81 mg, 0.17 mmol) in DMF (2 mL) and H$_2$O (0.006 mL) at −20° C. was added NaHCO$_3$ (22 mg, 0.26 mmol). NBS (31 mg, 0.17 mmol) was quickly added and mixture was stirred at room temperature in the dark. After 15 min, the reaction was diluted with ethyl acetate (20 mL) and washed with saturated Na$_2$SO$_3$ (1×10 mL) and H$_2$O (1×10 mL). The organic fraction was dried over anhydrous Na$_2$SO$_4$, filtered, and concentrated in vacuo. Rapid purification by flash chromatography (1:1 hexanes/ethyl acetate) gave 52 mg (60% yield) of bmk silyl ether, which was used without further purification.

To a solution of the bmk silyl ether (18 mg, 0.035 mmol) in THF (1 mL) at 0° C. was added 1 N HBr (0.33 mL). After stirring for 30 min at 0° C. and 2 h at room temperature, the reaction was diluted with ethyl acetate (5 mL) and washed with saturated NaHCO$_3$ (1×5 mL) and H$_2$O (1×5 mL). The organic fraction was dried over anhydrous Na$_2$SO$_4$, filtered, and concentrated in vacuo. Purification by preparative HPLC (30-100% MeOH gradient over 15 min; 10 mL/min flow rate; retention time for 3 was 11.9 min), afforded the desired bmk 3 as an off-white solid: $^1$H NMR (400 MHz, CDCl$_3$) δ8.36 (s, 1H), 7.38 (br s, 4H), 5.0 (br s, 2H), 4.66 (t, J=5.6 Hz, 2H), 3.74 (s, 2H), 3.46 (m, 2H), 2.49 (s, 3H), 2.12-2.07 (m, 2H); $^{13}$C NMR (100 MHz, CDCl$_3$) δ185.4, 159.0, 155.6, 151.9, 139.9, 130.4, 130.3, 129.5, 128.1, 124.7, 102.1, 57.7, 40.5, 34.3, 32.9, 21.4; ESI-MS 405 [M+2]$^+$, 403 [M]$^+$; HRMS (EI) Calcd for C$_{18}$H$_{19}$BrN$_4$O$_2$ 402.0691. found 402.0699.

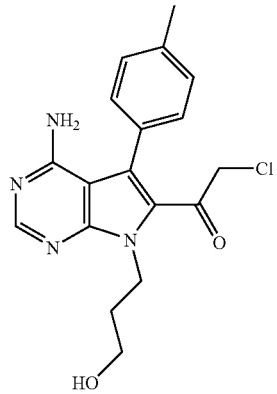

4

Chloromethyl Ketone (cmk) 4.

To a solution of enol ether 2 (262 mg, 0.56 mmol) in MeCN (6 mL) and H$_2$O (0.05 mL) was added NaHCO$_3$ (94 mg, 1.12 mmol). NCS (89 mg, 0.67 mmol) was quickly added and mixture was stirred at room temperature in the dark. After 1 h, the reaction was diluted with ethyl acetate (20 mL) and washed with saturated Na$_2$SO$_3$ (1×10 mL) and brine (1×10 mL). The organic fraction was dried over anhydrous Na$_2$SO$_4$, filtered, and concentrated in vacuo. Rapid purification by flash chromatography (1:1 hexanes/ethyl acetate) gave 101 mg (40% yield) of cmk silyl ether, which was used immediately in the next reaction.

To a solution of the cmk silyl ether (32 mg, 0.046 mmol) in THF (1 mL) at 0° C. was added 1 N HCl (0.33 mL). After stirring for 30 min at 0° C. and 2 h at room temperature, the reaction was diluted with ethyl acetate (5 mL) and washed with saturated NaHCO$_3$ (1×5 mL) and brine (1×5 mL). The organic fraction was dried over anhydrous Na$_2$SO$_4$, filtered, and concentrated in vacuo. Purification by preparative HPLC (30-100% MeOH gradient over 15 min; 10 mL/min flow rate; retention time for 4 was 11.2 min), afforded the desired cmk 4 as a white solid: $^1$H NMR (400 MHz, CDCl$_3$) δ8.36 (s, 1H), 7.37 (d, 2H), 7.36 (d, 2H), 5.0 (br s, 2H), 4.67 (t, J=6.0 Hz, 2H), 3.93 (s, 2H), 3.40 (m, 2H), 2.49 (s, 3H), 2.10 (m, 2H); $^{13}$C NMR (100 MHz, CDCl$_3$) δ 185.1, 159.1, 155.8, 151.8, 140.0, 130.5, 130.3, 129.5, 128.1, 124.8, 102.1, 57.7, 48.2, 40.6, 32.9, 21.4; ESI-MS 361 [M+2]+, 359 [M]+; HRMS (EI) Calcd for $C_{18}H_{19}ClN_4O_2$ 358.1196. found 358.1196.

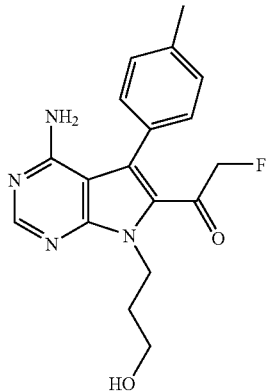

Fluoromethyl Ketone (fmk) 5.

To a solution of bmk silyl ether (22 mg, 0.042 mmol) in MeCN (1 mL) and DMF (0.1 mL) was added KF (19 mg, 0.327 mmol). [bmim][BF4] (0.15 mL) was added followed by H2O (0.034 mL) and the reaction was brought to 60° C. After 3 h, the reaction was diluted with ethyl acetate (5 mL) and washed with H2O (1×5 mL). The organic fraction was dried over anhydrous Na2SO4, filtered, and concentrated in vacuo. Rapid purification by flash chromatography (1:1 hexanes/ethyl acetate) gave 7.2 mg (40% yield) of fmk silyl ether, which was used immediately in the next step.

To a solution of the fmk silyl ether (7.2 mg, 0.016 mmol) in THF (1 mL) at 0° C. was added 1 N HCl (0.35 mL). After stirring for 3 h at 0° C., the reaction was diluted with ethyl acetate (5 mL) and washed with saturated NaHCO3 (1×5 mL) and brine (1×5 mL). The organic fraction was dried over anhydrous Na2SO4, filtered, and concentrated in vacuo. Purification by preparative HPLC (30-100% MeOH gradient over 15 min; 10 mL/min flow rate; retention time for 5 was 10.3 min), afforded the desired fmk 5 as a white solid: $^1$H NMR (400 MHz, CDCl3) δ 8.37 (s, 1H), 7.38 (d, 2H), 7.34 (d, 2H), 4.95 (br s, 2H), 4.72 (t, J=5.6 Hz, 2H), 4.68-4.56 (d, $J_{HF}$=47 Hz, 2H), 3.46 (m, 2H), 2.49 (s, 3H), 2.13-2.08 (m, 2H); $^{13}$C NMR (100 MHz, CDCl3) (partial) δ 155.8, 140.0, 130.5, 129.3, 57.7, 40.7, 32.9, 21.4; HRMS (EI) Calcd for $C_{18}H_{19}FN_4O_2$ 342.1492. found 342.1502.

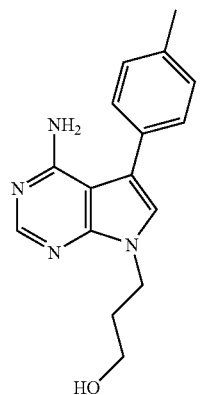

Pyrrolo[2,3-d]pyrimidine 6.

To a solution of 1 (49 mg, 0.123 mmol) in THF (3 mL) at 0° C. was added 1 N HCl (0.5 mL). After stirring for 1 h 30 min at 0° C. and 30 min at room temperature, the reaction mixture was diluted with ethyl acetate (10 mL) and washed with saturated NaHCO3 (1×10 mL) and brine (1×10 mL). The organic fraction was dried over anhydrous Na2SO4, filtered, and concentrated in vacuo to provide 35 mg (100% yield) of 6 as a clear film; Compound 6 was found to be 99% pure by HPLC (30-100% MeOH gradient over 15 min; 0.75 mL/min flow rate; retention time for 6 was 9.3 min); $^1$H NMR (400 MHz, CDCl3) δ 8.27 (s, 1H), 7.36 (d, J=8.0 Hz, 2H), 7.27 (d, J=8.3 Hz, 2H), 6.91 (s, 1H), 5.4 (br s, 2H), 4.35 (t, J=6.0 Hz, 2H), 3.46 (t, J=5.6 Hz, 2H), 2.41 (s, 2H), 1.96 (m, 2H); $^{13}$C NMR (100 MHz, CDCl3) δ 157.2, 151.8, 150.6, 137.0, 131.6, 129.7, 128.6, 122.7, 116.6, 100.7, 57.5, 40.6, 33.3, 21.1; HRMS (EI) Calcd for $C_{16}H_{18}N_4O_2$ 282.1480. found 282.1477.

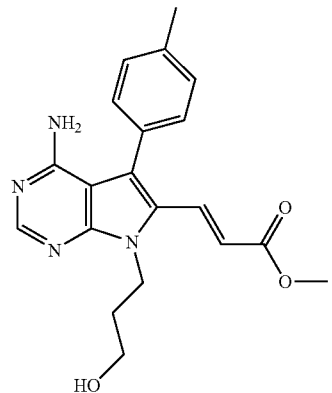

Methyl Enoate 2.

To bromide 1 (137 mg, 0.29 mmol) in DMF (2 mL) and Et3N (0.20 mL, 1.44 mmol) was added palladium acetate (22.5 mg, 0.1 mmol). The mixture was degassed by two cycles of freeze-pump-thaw and tri-o-tolylphosphine (53 mg, 0.17 mmol) was added, followed by methyl acrylate (0.206 mL, 2.90 mmol). The mixture was heated to 100° C. in a sealed-tube reaction vessel. After 4 h, the mixture was concentrated in vacuo and the crude product was rapidly purified by flash chromatography (1:1 hexanes/ethyl acetate) to give 70 mg (51% yield) of crude methyl enoate silyl ether, which was used without further purification.

To a solution of the silyl ether (22 mg, 0.046 mmol) in THF (2 mL) at 0° C. was added 1 N HCl (0.3 mL). After stirring for 1 h 30 min at 0° C. and 1 h at room temperature, the reaction was diluted with ethyl acetate (5 mL) and washed with saturated NaHCO3 (1×5 mL) and brine (1×5 mL). The organic fraction was dried over anhydrous Na2SO4, filtered, and concentrated in vacuo. Purification by preparative TLC (2×0.5 mm plates; 10% MeOH/CH2Cl2) afforded 7.3 mg (46% yield) of methyl enoate 7 as a slightly yellow solid; $^1$H NMR (400 MHz, CDCl3) δ 8.29 (s, 1H), 7.61 (d, J=16.4 Hz, 1H), 7.31 (d, 2H), 7.30 (d, 2H), 6.05 (d, J=16.4 Hz, 1H), 5.2 (br s, 2H), 4.53 (t, J=5.6 Hz, 2H), 3.73 (s, 3H), 3.46 (m, 2H), 2.45 (s, 3H), 2.01 (m, 2H).

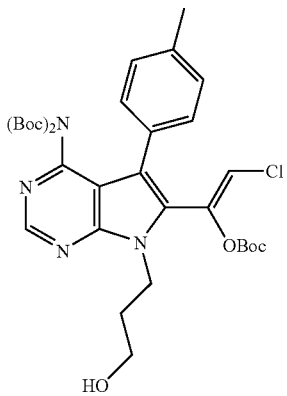

Enol Carbonate 8.

To a solution of cmk silyl ether (50 mg, 0.11 mmol) in THF (0.60 mL) was added (Boc)$_2$O (210 mg, 0.42 mmol), followed by DMAP (6.5 mg, 0.053 mmol). After stirring for 2 h 40 min at room temperature, the mixture was diluted with ethyl acetate (5 mL) and washed with 10% citrate buffer pH 4.0 (1×5 mL) and brine (1×5 mL). The organic fraction was dried over anhydrous Na$_2$SO$_4$, filtered, and concentrated in vacuo to provide 62 mg of the crude enol carbonate silyl ether. This compound was dissolved in THF (1 mL) and treated at 0° C. with 1 N HCl (0.33 mL). After 3 h, the reaction was diluted with ethyl acetate (5 mL) and washed with saturated NaHCO$_3$ (1×5 mL) and brine (1×5 mL). The organic fraction was dried over anhydrous Na$_2$SO$_4$, concentrated, and purified by flash chromatography (50-100% hexanes/ethyl acetate) to provide the enol carbonate 8 (49 mg, 84% over two steps): R$_f$ 0.40 (1:1 hexanes/ethyl acetate); $^1$H NMR (400 MHz, CDCl$_3$) δ 8.83 (s, 1H), 7.35 (d, J=8 Hz, 2H), 7.16 (d, J=8 Hz, 2H), 5.88 (s, 1H), 4.50 (t, 2H), 3.52 (t, 3H), 2.40 (s, 3H), 2.0 (m, 2H), 1.49 (s, 9H), 1.28 (s, 18H).

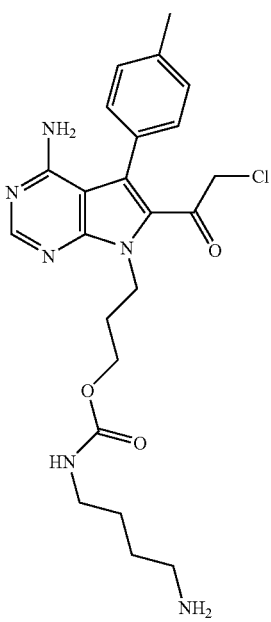

Carbamate 9.

Enol carbonate 8 (51 mg, 0.077 mmol) was azeotropically dried with toluene under high vacuum and dissolved in CH$_2$Cl$_2$ (0.5 mL). DIPEA (0.015 mL, 0.085 mmol) was added, followed by CDI (14 mg, 0.085 mmol). After stirring for 1 h at room temperature, N-Boc-1,4-diaminobutane (16 mg, 0.085 mmol) was added. After 5 h 40 min, and additional 1.1 equivalents of N-Boc-1,4-diaminobutane (16 mg, 0.085 mmol) was added. After 8 h, the reaction was diluted with ethyl acetate (5 mL) and washed with 10% sodium citrate buffer (1×5 mL) and brine (1×5 mL). The organic fraction was dried over anhydrous Na$_2$SO$_4$, filtered, and concentrated in vacuo. Rapid purification by flash chromatography (1:1-2:1 ethyl acetate/hexanes) gave 43 mg of the boc-protected carbamate, which was used immediately in the next step.

To a solution of the boc-protected carbamate (43 mg, 0.056 mmol) in CH$_2$Cl$_2$ (0.8 mL) at 0° C. was added TFA (0.7 mL). After warming to room temperature and stirring for 3 h, solvents were removed in vacuo to yield 26 mg (73% over three steps) of carbamate 9 as a white solid; ESI-MS 497 [M+2+Na]$^+$, 495 [M+Na]$^+$, 475 [M+2]$^+$, 473 [M]$^+$.

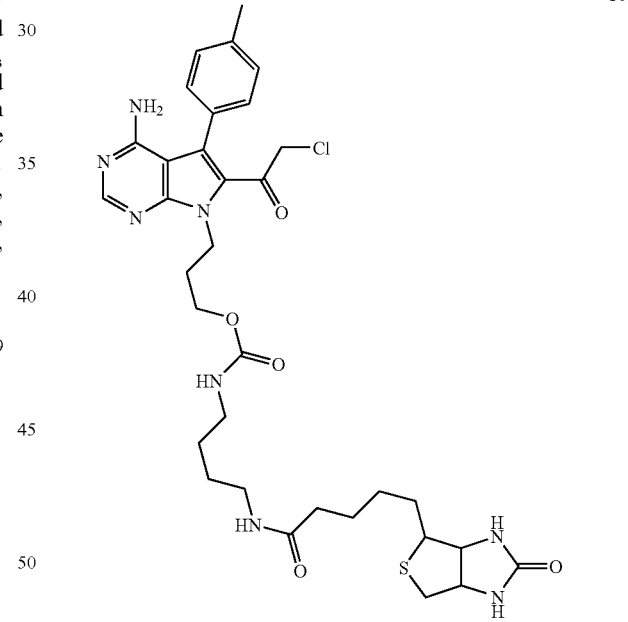

Biotin Cmk 10.

To a solution of carbamate 9 (9 mg, 0.019 mmol) in DMF (0.1 mL) at room temperature was added Biotin-NHS (13 mg, 0.038 mmol), followed by DIPEA (0.007 mL, 0.038 mmol). After 24 h, the crude mixture was purified directly by preparative HPLC (30-100% MeOH gradient over 15 min; 10 mL/min flow rate; retention time for 10 was 12.2 min) to afford 9 mg (70% yield) of the desired biotin cmk 10 as a white solid; ESI-MS 723 [M+2+Na]$^+$, 721 [M+Na]$^+$.

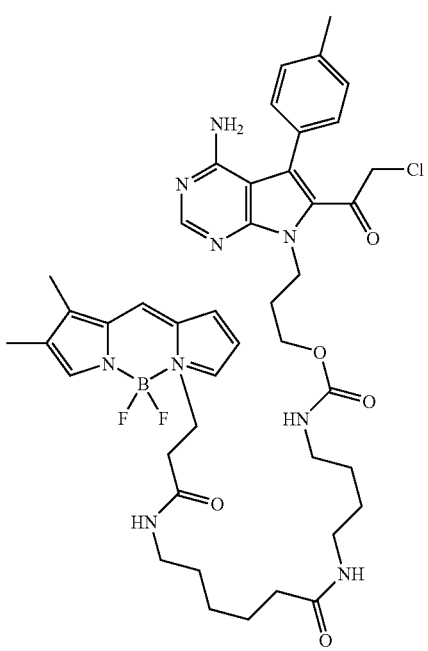

Bodipy Cmk 11.

To a solution of carbamate 9 (4 mg, 0.008 mmol) in DMF (0.1 mL) at room temperature was added Bodipy-NHS (5 mg, 0.009 mmol), followed by DIPEA (0.003 mL, 0.016 mmol). After 24 b in the dark, the solvents were removed and the mixture was purified by flash chromatography (10:1 CH$_2$Cl$_2$/MeOH) to give bodipy cmk 11 as a red solid in quantitative yield; ESI-MS 882 [M+Na]$^+$; $^1$H NMR (400 MHz, CDCl$_3$) δ11.2 (br s, 2H), 8.23 (s, 1H), 8.00 (s, 1H), 7.37 (d, J=8 Hz, 2H), 7.30 (d, J=8.4 Hz, 2H), 7.1 (s, 1H), 6.86 (d, J=3.6 Hz, 1H), 6.23 (d, J=3.6 Hz, 1H), 6.10 (s, 1H), 5.80 (m, 2H), 4.70 (t, 2H), 4.04 (t, 2H), 3.92 (s, 2H), 3.68 (m, 2H), 3.25-3.06 (m, 6H), 2.68 (s), 2.60 (t, J=7.6 Hz, 2H), 2.53 (s, 3H), 2.46 (s, 3H), 2.23 (s, 3H), 2.1 (m, 2H), 1.46-1.37 (m, 10H).

Preparation of Enone 15.

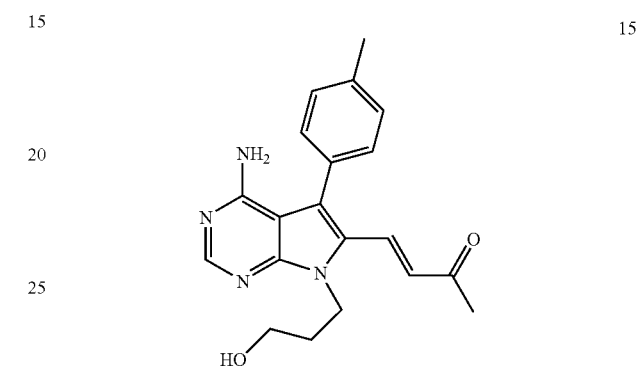

Enone 15 was prepared according to the following scheme:

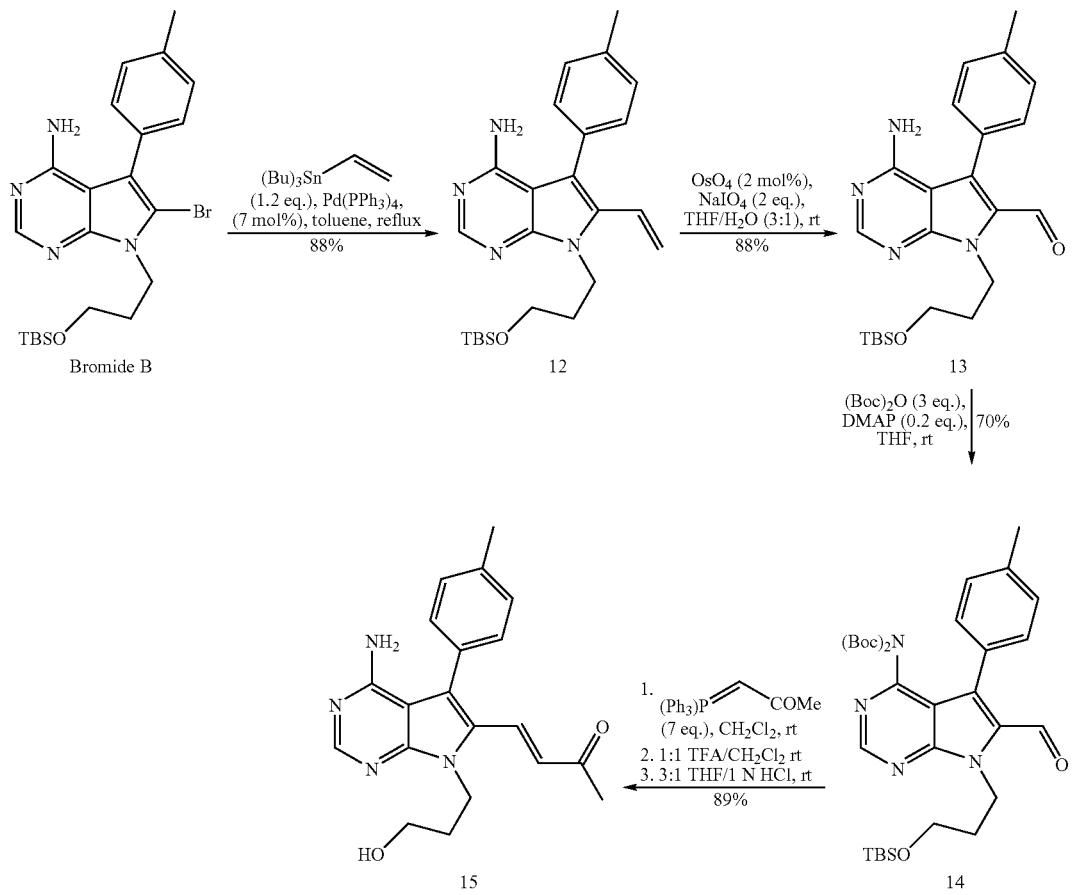

Experimental Methods:

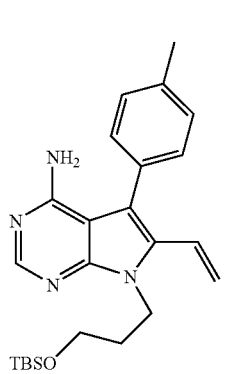

12

Vinyl 12.

To a solution of bromide B (350 mg, 0.74 mmol) in toluene (16 mL) was added tributyl(vinyl)tin (0.260 mL, 0.89 mmol). Argon gas was bubbled through the solution for 5 min. Tetrakis(triphenylphosphine)palladium (60 mg, 0.052 mmol) was quickly added and the mixture was refluxed for 10 h. The solvent was removed in vacuo and the crude product was purified by flash chromatography (2:1 ethyl acetate/hexanes) to give vinyl 12 (271 mg, 88% yield): $R_f$ 0.45 (100% ethyl acetate); $^1$H NMR (400 MHz, CDCl$_3$) δ 8.28 (s, 1H), 7.31 (d, J=8.0 Hz, 2H), 7.26 (d, J=8.0 Hz, 2H), 6.66 (dd, 18 Hz, 12 Hz, 1H), 5.44 (dd, J=18 Hz, 1.2 Hz, 1H), 5.24 (dd, J=12 Hz, 1.2 Hz, 1H), 4.89 (br s, 2H), 4.37 (t, 2H), 3.73 (t, 2H), 2.42 (s, 3H), 2.053 (m, 2H), 0.89 (s, 9H), 0.05 (s, 6H); $^{13}$C NMR (100 MHz, CDCl$_3$) δ 1156.7, 152.0, 137.4, 131.8, 130.9, 130.4, 129.6, 124.9, 118.1, 114.4, 102.3, 60.3, 39.8, 33.2, 25.9, 21.2, 18.2.

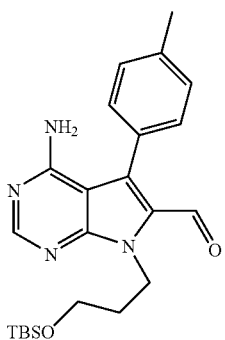

13

Aldehyde 13.

To a solution of vinyl 12 (50 mg, 0.12 mmol) in 3:1 THF/H$_2$O (1 mL) was added OsO$_4$ (2.5 wt. % in t-butanol, 0.030 mL, 0.0024 mmol). The mixture was stirred for 10 min at room temperature, during which time the solution turned dark brown. NaIO$_4$ (45 mg, 0.21 mmol) in H$_2$O (0.20 mL) was added dropwise over a period of 10 min, during which time the solution turned yellow and a white precipitate formed. After 1 h, the reaction mixture was diluted with ethyl acetate (10 mL) and washed with sat. Na$_2$SO$_3$ (1×10 mL). The organic fraction was dried over Na$_2$SO$_4$, filtered, and concentrated in vacuo. Purification by flash chromatography (2:1 ethyl acetate/hexanes) gave 43 mg (86% yield) of aldehyde 13: $R_f$ 0.51 (100% ethyl acetate); $^1$H NMR (400 MHz, CDCl$_3$) δ 9.63 (s, 1H), 8.41 (s, 1H), 7.38 (d, J=8 Hz, 2H), 7.33 (d, J=8 Hz, 2H), 5.1 (br s, 2H), 4.72 (t, 2H), 3.73 (t, 2H), 2.45 (s, 3H), 2.04 (m, 2H), 0.89 (s, 9H), 0.05 (s, 6H).

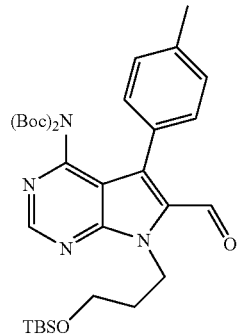

14

Diboc-aldehyde 14.

To a solution of aldehyde 13 (135 mg, 0.32 mmol) in THF (3 mL) was added (Boc)$_2$O (207 mg, 0.95 mmol). DMAP (8 mg, 0.064 mmol) was quickly added and the mixture was stirred for 2 h at room temperature. The reaction mixture was diluted with ethyl acetate (10 mL) and washed with 0.5 N HCl (1×10 mL) followed by brine (1×10 mL). The organic fraction was dried over Na$_2$SO$_4$, filtered, and concentrated in vacuo. Purification by flash chromatography (1:6 ethyl acetate/hexanes) afforded the desired diboc-aldehyde 14 (140 mg, 70% yield): $R_f$ 0.75 (1:1 ethyl acetate/hexanes); $^1$H NMR (400 MHz, CDCl$_3$) δ 9.84 (s, 1H), 8.96 (s, 1H), 7.34 (d, J=8 Hz, 2H), 7.26 (d, J=8 Hz, 2H), 4.82 (t, 2H), 3.74 (t, 2H), 2.44 (s, 3H), 2.05 (m, 2H), 1.31 (s, 18H), 0.92 (s, 9H), 0.06 (s, 6H); $^{13}$C NMR (100 MHz, CDCl$_3$) δ 184, 156.2, 155.4, 155.1, 150.3, 131.7, 130.3, 128.7, 113.3, 94.6, 83.6, 60.9, 41.8, 33.8, 28.8, 28.2, 28.1, 27.9, 27.2, 26.3, 25.9.

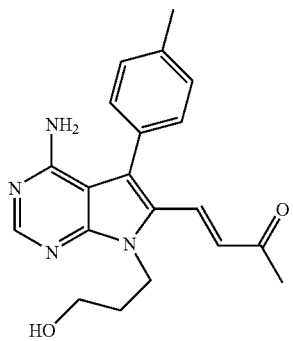

15

Enone 15.

To a solution of diboc-aldehyde 14 (23 mg, 0.037 mmol) in CH$_2$Cl$_2$ (0.5 mL) was added 1-triphenyl-phosphoranylidene-2-propanone (42 mg, 0.132 mmol) and the mixture was stirred at room temperature. After 2 h, another 3.5 equivalents of 1-triphenyl-phosphoranylidene-2-propanone (42 mg) was added and the reaction mixture was stirred for an additional 5 h at room temperature. The solvent was removed in vacuo and the crude product was purified by flash chromatography (1:4 ethyl acetate/hexanes) to give the desired diboc-enone, which was used immediately in the next reaction.

To a solution of the diboc-enone (21 mg, 0.03 mmol) in CH$_2$Cl$_2$ (0.25 mL) was added TFA (0.25 mL). After stirring for 2 h at room temperature, the solvent was removed in vacuo and the crude product was dissolved in 3:1 THF/1 N HCl (1.3 mL). After 3 h, the reaction mixture was diluted with CH$_2$Cl$_2$ (5 mL) and washed with saturated NaHCO$_3$ (1×5 mL) followed by brine (1×5 mL). The organic fraction was dried over Na$_2$SO$_4$, filtered, and concentrated in vacuo. Purification by flash chromatography (1:20 MeOH/CH$_2$Cl$_2$) gave enone 15 (9.6 mg, 89% yield) as a yellow solid: $R_f$ 0.20 (1:20 MeOH/CH$_2$Cl$_2$); $^1$H NMR (400 MHz, CDCl$_3$) δ 8.29 (s, 1H), 7.41 (d, J=16 Hz, 1H), 7.33 (d, J=8 Hz, 2H), 7.29 (d, J=8 Hz, 2H), 6.38 (d, J=16 Hz, 1H), 5.20 (br s, 2H), 4.53 (t, 2H), 3.48 (t, 2H), 2.45 (s, 3H), 2.20 (s, 3H), 2.01 (m, 2H); ESI-MS 351 [M+H]$^+$.
Preparation of Propargylamine-fmk 18
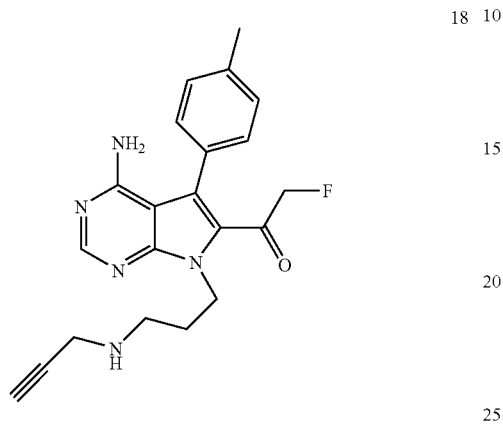
Propargylamine-fmk 18 was prepared by the following scheme:
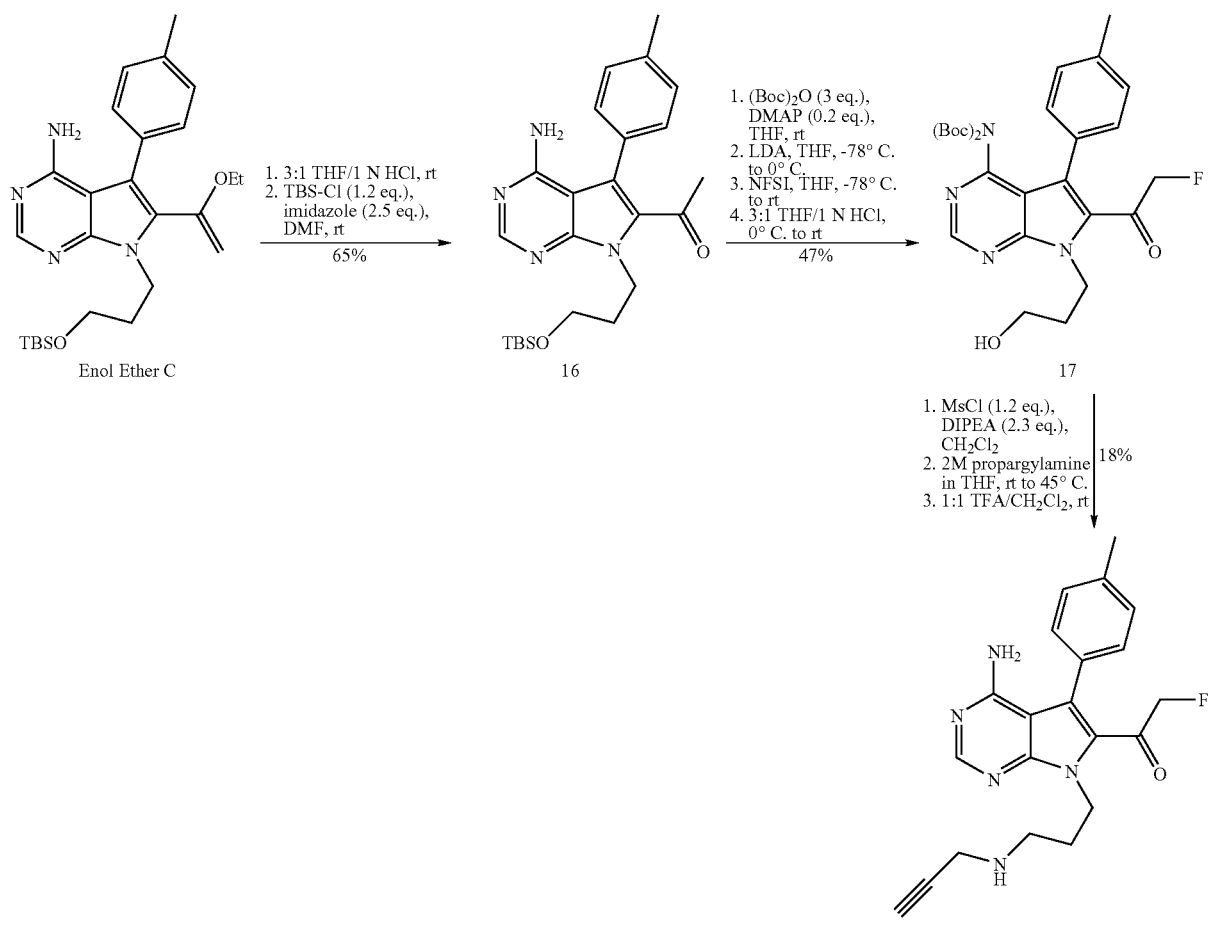

Experimental Methods:

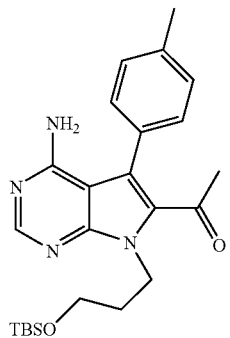

16

Ketone 16.

To a solution of enol ether C (1.46 g, 3.07 mmol) in THF (10 mL) was added 1N HCl (3 mL). After stirring for 12 h at room temperature, the reaction mixture was diluted with ethyl acetate (50 mL) and washed with saturated NaHCO$_3$ (1×200 mL). The crude product was extracted from the organic fraction with 1 N HCl (2×150 mL). The acidic aqueous fraction was brought to pH~8 with NaOH and then extracted with ethyl acetate (2×150 mL). The combined organic fractions were dried over Na$_2$SO$_4$, filtered, and concentrated in vacuo to give 850 mg (85% yield) of the deprotected ketone as an off-white solid. The crude product was used in the next reaction without further purification.

To a solution of the crude deprotected ketone (850 mg, 2.62 mmol) in DMF (15 mL) was added imidazole (450 mg, 6.60 mmol) followed by TBS-Cl (474 mg, 3.14 mmol). After stirring for 12 h at room temperature, the reaction mixture was poured into 150 mL of 10% citrate buffer [pH=4.0] and extracted with ethyl acetate (1×200 mL). The organic fraction was washed with brine (1×200 mL), dried over Na$_2$SO$_4$, filtered, and concentrated in vacuo. Purification by flash chromatography (1:1 ethyl acetate/hexanes) provided ketone 16 (876 mg, 76% yield): R$_f$ 0.70 (100% ethyl acetate); $^1$H NMR (400 MHz, CDCl$_3$) δ 8.28 (s, 1H), 7.28 (s, 4H), 5.10 (br s, 2H), 4.60 (t, 2H), 3.66 (t, 2H), 2.41 (s, 3H), 1.94 (s, 3H), 0.85 (s, 9H), 0.05 (s, 6H); $^{13}$C NMR (100 MHz, CDCl$_3$) δ 192.0, 158.8, 154.9, 151.0, 138.8, 131.7, 130.1, 129.9, 129.7, 123.9, 102.0, 61.1, 41.3, 33.8, 30.9, 25.9, 21.3, 18.3.

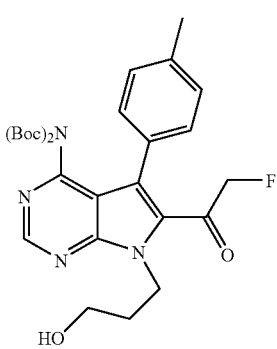

17 fmk 17.

To a solution of ketone 16 (780 mg, 1.78 mmol) in THF (10 mL) was added (Boc)$_2$O (1.16 g, 5.33 mmol). DMAP (44 mg, 0.36 mmol) was quickly added and the mixture was stirred for 2.5 h at room temperature. The reaction mixture was diluted with ethyl acetate (150 mL) and washed with 0.5 N HCl 1×200 mL) followed by brine (1×200 mL). The organic fraction was dried over Na$_2$SO$_4$, filtered, and concentrated in vacuo. Rapid purification by flash chromatography (1:5 ethyl acetate/hexanes) gave 884 mg (78% yield) of the desired diboc-ketone, which was used immediately in the next reaction.

A solution of THF (3 mL) and diisopropylamine (0.32 mL, 2.28 mmol) was cooled to −78° C. n-butyllithium (2.48 M in hexanes, 0.657 mL, 1.63 mmol) was added and the reaction mixture was warmed to 0° C. After 30 min, the reaction was cooled to −78° C. and the crude diboc-ketone (800 mg, 1.25 mmol) in THF (2.5 mL) was added dropwise. The reaction mixture was warmed to 0° C. for 20 min, then cooled to −78° C. N-fluorobenzenesulfonimide (631 mg, 2 mmol) in THF (2 mL) was added dropwise and the reaction mixture was warmed to room temperature. After 25 min, saturated NH$_4$Cl (1 mL) was added and the reaction mixture was poured into saturated NH$_4$Cl (150 mL) and extracted with ethyl acetate (1×100 mL). The organic fraction was dried over Na$_2$SO$_4$, filtered, and concentrated in vacuo. The crude product was dissolved in 3:1 THF/1 N HCl (12 mL). After 3 h at room temperature, the reaction mixture was diluted with ethyl acetate (100 mL) and washed with saturated NaHCO$_3$ (1×100 mL) followed by brine (1×100 mL). The organic fraction was dried over Na$_2$SO$_4$, filtered, and concentrated in vacuo. Purification by flash chromatography (1:4 ethyl acetate/hexanes) afforded the desired fmk 17 (408 mg, 60% yield over 2 steps) as an off-white solid: R$_f$ 0.50 (100% ethyl acetate); $^1$H NMR (400 MHz, CDCl$_3$) δ 8.91 (s, 1H), 7.24 (d, J=8 Hz, 2H), 7.20 (d, J=8 Hz, 2H), 4.70 (t, 2H), 4.60 (d, J$_{HF}$=47 Hz, 2H), 3.70 (t, 1H), 3.41 (m, 2H), 2.42 (s, 3H), 2.05 (m, 2H), 1.29 (s, 18H); $^{13}$C NMR (100 MHz, CDCl$_3$) δ 189.4 (d, J$_{CF}$=19 Hz), 155.25, 154.5, 154.0, 149.8, 139.2, 131.1, 129.7, 129.4, 128.75, 123.5, 114.2, 85.1, 83.5, 83.3, 58.2, 41.0, 32.9, 27.7, 21.2.

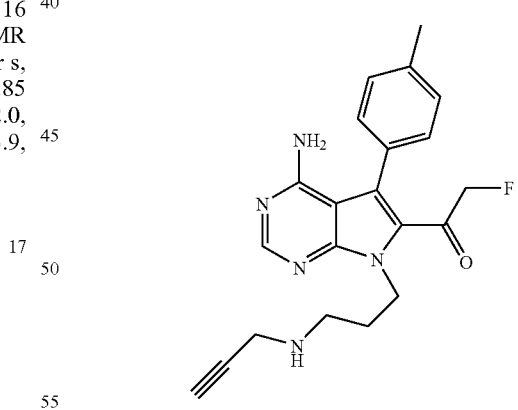

18 propargylamine-fmk 18.

To a solution of fmk 17 (75 mg, 0.14 mmol) in CH$_2$Cl$_2$ (3 mL) was added diisopropylethylamine (0.057 mL, 0.317 mmol) at 0° C. Methanesulfonyl chloride (1M in CH$_2$Cl$_2$, 0.17 mL, 0.17 mmol) was added and the reaction mixture was stirred at 0° C. After 30 min, the reaction mixture was diluted with ethyl acetate and washed with saturated NH$_4$Cl (1×10 mL) followed by brine (1×10 mL). The organic fraction was dried over Na$_2$SO$_4$, filtered, and concentrated in vacuo to give 82 mg (96% yield) of the mesylate-fmk, which was used in the next reaction without further purification.

To a solution of the crude mesylate-fmk (20 mg, 0.032 mmol) in THF (0.5 mL) was added propargylamine (4M in THF, 0.5 mL, 2 mmol). The mixture was stirred for 50 h at room temperature and then for 9 h at 45° C. The reaction mixture was diluted with ethyl acetate (10 mL) and washed with $H_2O$ (10 mL) followed by 10 mL of 10% citrate buffer [pH=4.0]. The organic fraction was dried over $Na_2SO_4$, filtered, and concentrated in vacuo. Purification by preparative layer chromatography (2:1 ethyl acetate/hexanes) afforded the desired diboc protected propargylamine-fmk (3.4 mg, 20% yield), which was dissolved in 1:1 $CH_2Cl_2$/TFA (2 mL) and stirred at room temperature. After 2.5 h, the solvent was removed in vacuo to give propargylamine-fmk 18 (3.3 mg, 92% yield): $^1$H NMR (400 MHz, CDCl$_3$) δ 11.1 (br s, 1H), 8.31 (s, 1H), 7.44 (d, J=8 Hz, 2H), 7.31 (d, J=8 Hz, 2H), 5.42 (br s, 2H), 4.76 (t, 2H), 4.67 (d, $J_{HF}$=47 Hz, 2H), 3.92 (s, 2H), 3.24 (m, 2H), 2.58 (s, 1H), 2.50 (s, 3H), 2.41 (m, 2H); ESI-MS 380 [M+H]$^+$.

Preparation of Compounds of Formula (V)

Compounds of Formula (V) may be prepared either by reaction of an appropriate iodooxindole with an alkylating agent to add a group $R^7$, followed by addition of an electrophilic moiety, or by first adding the electrophilic moiety to an iodooxindole and then adding the $R^7$ group. Examples of both types of processes are shown below.

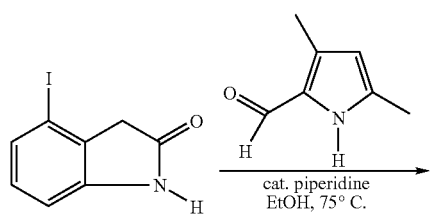

To a solution of 3,5-dimethylpyrrole 2-carboxaldehyde (34 mg, 0.276 mmol) in 1 mL EtOH was added 4-iodooxindole (56 mg, 0.216 mmol) and piperidine (2 μL, 0.02 mmol). The yellow mixture was heated and kept at 80° C. for 3 hours. The precipitated product was filtered to separate it from unreacted 3,5-dimethyl pyrrole 2-carboxaldehyde. The retentate was washed with cold ethanol (3×2 mL) and dried in a vacuum desiccator to yield 48 mg (61%) of the desired compound. $^1$H NMR (400 MHz, DMSO-d$_6$) δ: 13.36 (br s, 1H) 10.95 (br s, 1H), 8.71 (s, 1H), 7.47 (d, J=7.8 Hz, 1H), 6.94 (d, J=7.7 Hz, 1H), 6.84 (t, J=7.7 Hz, 1H), 6.09 (s, 1H), 2.34 (s, 3H), 2.31 (s, 3H). ESI-MS 387 (M+Na)$^+$

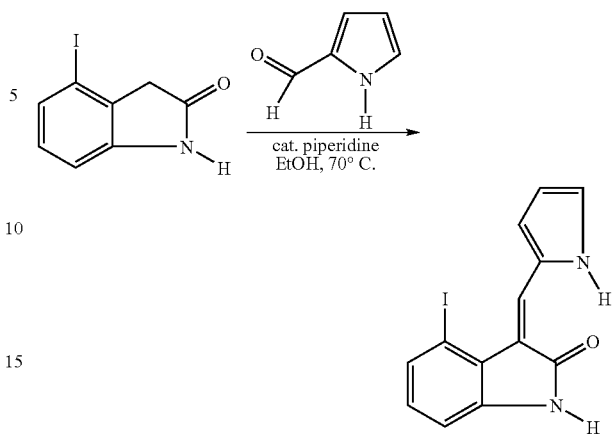

To a solution of 4-iodooxindole (97 mg, 0.375 mmol) in 1 mL EtOH was added 5-dimethylpyrrole 2-carboxaldehyde (46 mg, 0.484 mmol) and piperidine (2 μL, 0.02 mmol). The yellow mixture was heated and kept at 70° C. for 3 hours. The precipitated product was filtered to separate it from unreacted 3,5-dimethylpyrrole 2-carboxaldehyde. The retentate was washed with cold ethanol (3×2 mL) and dried in a vacuum desiccator to yield 112 mg (89%) of the desired compound. $^1$H NMR (400 MHz, DMSO-d6) δ: 13.48 (br s, 1H) 11.08 (br s, 1H), 8.72 (s, 1H), 7.49 (d, J=7.8 Hz, 1H), 7.44 (m, 1H), 6.92 (m, 3H), 6.41 (m, 1H). ESI-MS 359 (M+Na)$^+$, 360 (M+1+Na)$^+$

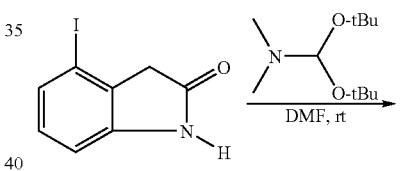

To a solution of 4-iodooxindole (187 mg, 0.722 mmol) in 1 mL dry DMF was added dimethylformamide di-tert-butyl acetal (300 μL, 1.25 mmol). The dark red mixture was stirred at room temperature for 16 hours under an Ar atmosphere (with balloon). Volatiles were removed under high vacuum and the brown residue diluted in EtOAc (5 mL), washed with water (2×5 mL) and brine (1×5 mL). The organic fraction was dried over anhydrous $Na_2SO_4$, filtered and concentrated in vacuo. Drying under high vacuum yielded 218 mg (96%) of isomers of the desired compound as a yellow powder. $^1$H NMR (400 MHz, DMSO-d6) δ: 10.13 (br s, 1H) 8.55 (s, 1H), 7.25 (d, J=7.9 Hz, 1H), 6.76 (d, J=7.6 Hz, 1H), 6.61 (d, J=7.9 Hz, 1H), 3.35 (br s, 6H). ESI-MS 315 (M+H)$^+$, 337 (M+Na)$^+$

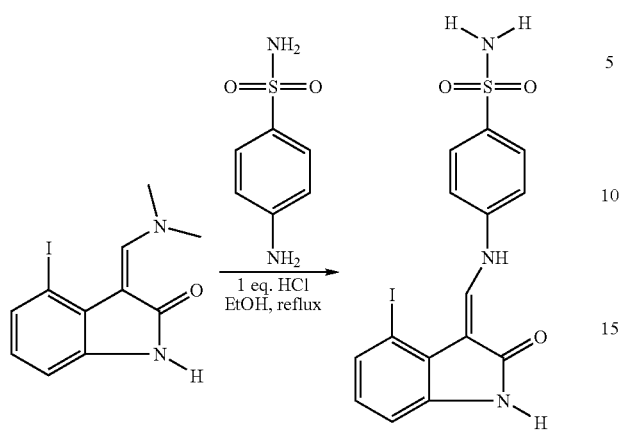
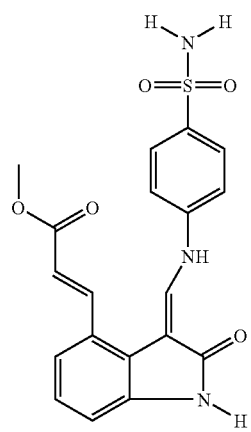

To a solution of 3-dimethylaminomethylene-4-iodooxindole (111 mg, 0.354 mmol) in 4 mL EtOH was added sulfanilamide (70 mg, 0.407 mmol) and 200 μL 15% aqueous HCl (v/v). The bright yellow solution was heated to reflux for 20 hours at which point a bright yellow precipitate in an orange solution was observed. The reaction mixture was filtered to separate the precipitated product from unreacted sulfanilamide. The retentate was washed with cold ethanol (3×3 mL) and dried in a vacuum desiccator to yield 119 mg (63%) of B41 as isomeric products as observed by $^1$H NMR. $^1$H NMR (400 MHz, DMSO-d6) δ: 11.39 (d, J=12.1 Hz, 1H), 10.86 (br s, 1H), 9.15 (d, J=11.9 Hz, 1H), 7.83 (d, J=8.5 Hz, 2H), 7.46 (d, J=8.5 Hz, 2H), 7.41 (d, J=7.9 Hz, 1H), 7.33 (br s, 2H), 6.94 (d, J=7.7 Hz, 1H), 6.84 (t, J=7.8 Hz, 1H). ESI-MS 464 (M+Na)$^+$

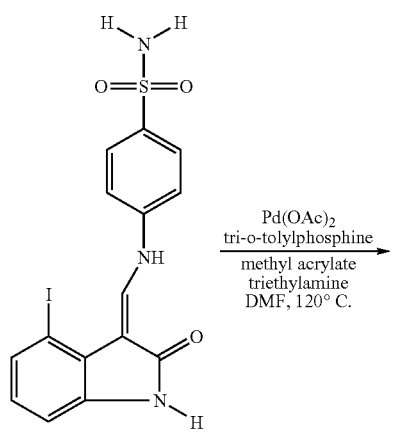

To a solution of the benzenesulfonamide prepared in the previous example (20 mg, 0.045 mmol) in 0.3 mL dry DMF at room temperature was added tri-ortho-tolylphosphine (9 mg, 0.030 mmol), palladium acetate (3 mg, 0.013 mmol), methyl acrylate (40 μL, 0.444 mmol), and triethylamine (20 μL, 0.144 mmol) under an Ar atmosphere (two needles, one for Ar to flow in and another for venting are connected to the reaction flask). A reflux condenser was connected to the flask containing the reaction mixture while still maintaining an active Ar flow into the reaction vessel. Under a passive Ar pressure, the reaction flask was submerged into a liquid $N_2$ bath for 3-5 minutes to freeze the reaction mixture. $O_2$ was removed by exposing the frozen mixture in liquid $N_2$ to high vacuum for 20-30 seconds. The reaction mixture was then thawed back to room temperature under an Ar atmosphere. The freeze, pump, thaw cycle was repeated two more times. During the last thaw step, the reaction vessel was tightly sealed, put under a passive Ar atmosphere (via an Ar balloon) and water was circulated through the reflux condenser. After the reaction mixture was heated at 120° C. in an oil bath for 5 hours, volatiles were removed from the reaction mixture under high vacuum overnight. The resulting brown residue was diluted in ethanol and filtered to isolate the precipitated product as a dark yellow solid. Yield was not quantitated for this product. $^1$H NMR (400 MHz, DMSO-d6) δ: 11.40 (d, J=12.2 Hz, 1H), 10.83 (br s, 1H), 8.23 (d, J=12.1 Hz, 1H), 8.13 (d, J=15.6 Hz, 1H), 7.83 (d, J=8.6 Hz, 2H), 7.48 (d, J=8.8 Hz, 2H), 7.31 (br s, 2H), 7.27 (d, J=7.9 Hz, 1H), 7.11 (t, J=7.8 Hz, 1H), 6.93 (d, J=7.6 Hz, 1H) 6.58 (d, J=15.7 Hz, 1H), 3.80 (s, 3H). ESI-MS 422 (M+Na)$^+$

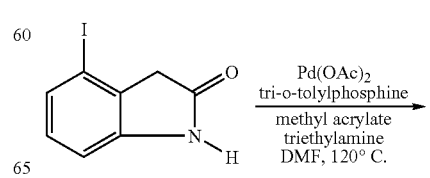

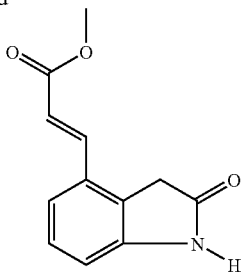

To a solution of 4-iodooxindole (104 mg, 0.402 mmol) in 2.5 mL dry DMF at room temperature was added tri-ortho-tolylphosphine (71 mg, 0.233 mmol), palladium acetate (26 mg, 0.116 mmol), methyl acrylate (0.35 mL, 3.89 mmol), and triethylamine (0.160 mL, 1.15 mmol) under an Ar atmosphere (two needles, one for Ar to flow in and another for venting are connected to the reaction flask). A reflux condenser was connected to the flask containing the reaction mixture while still maintaining an active Ar flow into the reaction vessel. Under a passive Ar pressure, the reaction flask was submerged into a liquid $N_2$ bath for 3-5 minutes to freeze the reaction mixture. $O_2$ was removed by exposing the frozen mixture in liquid $N_2$ to high vacuum for 20-30 seconds. The reaction mixture was then thawed back to room temperature under an Ar atmosphere. The freeze, pump, thaw cycle was repeated two more times. During the last thaw step, the reaction vessel was tightly sealed, put under a passive Ar atmosphere (via an Ar balloon) and water was circulated through the reflux condenser. After the reaction mixture was heated at 120° C. in an oil bath for 5 hours, volatiles were removed from the reaction mixture under high vacuum overnight. The resulting brown residue was diluted in ethyl acetate (30 mL) and washed with water (2×30 mL) and brine (1×30 mL). The organic fraction was dried over anhydrous $Na_2SO_4$, filtered and concentrated in vacuo. Purification by column chromatography on silica gel (1:1 hexanes/ethyl acetate) yielded 46.8 mg (54%) of the desired compound as a brown solid. $^1$H NMR (400 MHz, $CDCl_3$) δ: 8.01 (br s, 1H) 7.65 (d, J=16 Hz, 1H), 7.24 (m, 2H), 6.90 (d, J=7.0 Hz, 1H), 6.41 (d, J=16 Hz, 1H), 3.83 (s, 3H), 3.63 (s, 2H). ESI-MS 240 (M+Na)$^+$, 457 (2M+Na)$^+$

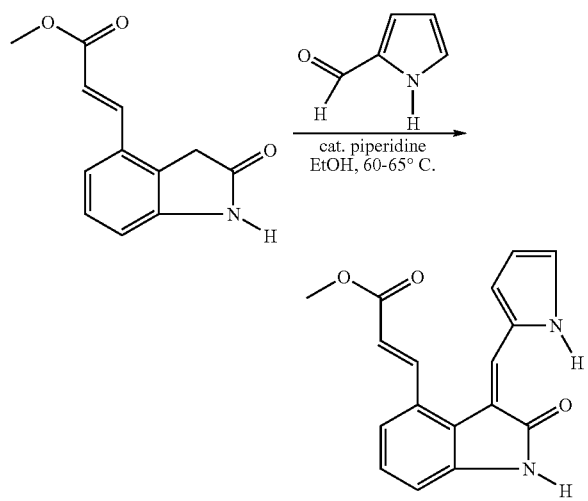

To a solution of 4-enoateoxindole prepared as above (16 mg, 0.074 mmol) in 1 mL EtOH was added pyrrole 2-carbox-aldehyde (9 mg, 0.095 mmol) and piperidine (0.6 μL, 0.006 mmol). The orange mixture was heated and kept at 65° C. for 16 hours. The reaction mixture was diluted with ethyl acetate (5 mL) and washed with water (2×5 mL) and brine (1×5 mL). The organic fraction was dried over anhydrous $Na_2SO_4$, filtered and concentrated in vacuo. Purification by preparative TLC (2:1 hexanes/ethyl acetate) yielded 5.6 mg (26%) of the desired compound. $^1$H NMR (400 MHz, $CDCl_3$) δ: 13.38 (br s, 1H) 8.26 (d, J=15.7 Hz, 1H), 7.86 (br s, 1H), 7.56 (s, 1H), 7.16 (m, 3H), 6.91 (d, J=7.3 Hz, 1H), 6.85 (m, 1H), 6.44 (d, J=15.8 Hz, 1H), 6.41 (m, 1H), 3.88 (s, 3H). ESI-MS 317 (M+Na)$^+$

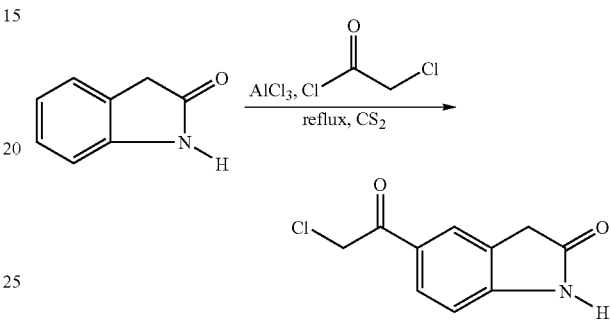

To a solution of $AlCl_3$ (6.28 g, 47.1 mmol) in 20 mL of dry carbon disulfide was added chloroacetylchloride (800 μL, 10.0 mmol) at room temperature. Oxindole (1.02 g, 7.7 mmol) in 10 mL dry carbon disulfide was added portionwise via a syringe for 5 minutes. The reaction mixture was stirred at RT for an additional 10 min, then refluxed (40-50° C.) for 1 hour. The reaction was cooled, added to ice and the beige precipitate filtered, washed with cold water and dried in a vacuum desiccator to afford 501 mg (31%) of the desired compound. $^1$H NMR (400 MHz, DMSO-d6) δ: 10.82 (s, 1H), 7.89 (dd, J=1.8 Hz, 8.2 Hz, 1H), 7.83 (s, 1H), 6.93 (d, J=8.2 Hz, 1H), 5.08 (s, 2H), 3.32 (s, 2H). ESI-MS 232 (M+Na)$^+$, 234 (M+2+Na)$^+$

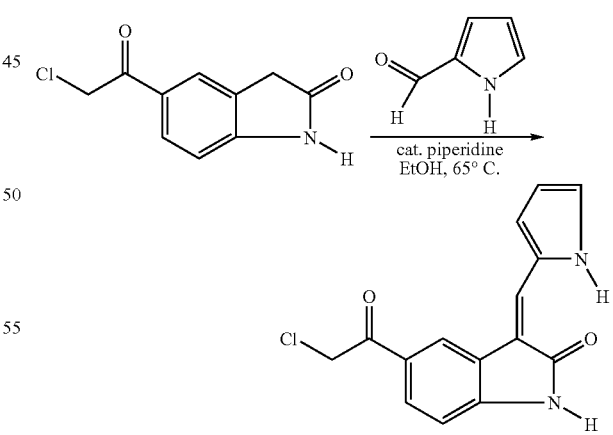

To a solution of pyrrole 2-carboxaldehyde (60 mg, 0.627 mmol) in 3 mL EtOH was added 5-chloroacetyloxindole (104 mg, 0.496 mmol) and piperidine (4 μL, 0.04 mmol). The yellow mixture was heated and kept at 65° C. for 5 hours. The reaction mixture was filtered to remove unreacted oxoindole. The filtrate was concentrated and purified by column chromatography on silica gel (1:1 hexanes/ethyl acetate) to yield 13 mg (9%) of the desired compound. $^1$H NMR (400 MHz, DMSO-d6) δ: 13.22 (br s, 1H) 11.34 (s, 1H), 8.34 (s, 1H), 7.98 (s, 1H), 7.85 (dd, J=1.3 Hz, 8.2 Hz, 1H), 7.43 (s, 1H), 7.02 (d, J=8.2 Hz, 1H), 6.94 (s, 1H), 6.42 (m, 1H), 5.17 (s, 2H). ESI-MS 309 (M+Na)$^+$, 311 (M+2+Na)$^+$, 595 (2M+23)$^+$

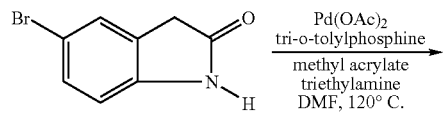

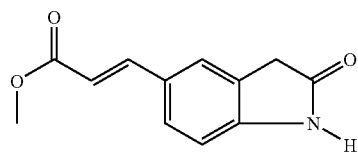

To a solution of 5-bromooxindole (340 mg, 1.603 mmol) in 10 mL dry DMF at room temperature was added tri-ortho-tolylphosphine (304 mg, 0.999 mmol), palladium acetate (114 mg, 0.508 mmol), methyl acrylate (1.4 mL, 15.55 mmol), and triethylamine (0.650 mL, 4.68 mmol) under an Ar atmosphere (two needles, one for Ar to flow in and another for venting are connected to the reaction flask). A reflux condenser was connected to the flask containing the reaction mixture while still maintaining an active Ar flow into the reaction vessel. Under a passive Ar pressure, the reaction flask was submerged into a liquid $N_2$ bath for 3-5 minutes to freeze the reaction mixture. $O_2$ was removed by exposing the frozen mixture in liquid $N_2$ to high vacuum for 20-30 seconds. The reaction mixture was then thawed back to room temperature under an Ar atmosphere. The freeze, pump, thaw cycle was repeated two more times. During the last thaw step, the reaction vessel was tightly sealed, put under a passive Ar atmosphere (via an Ar balloon) and water was circulated through the reflux condenser. After the reaction mixture was heated at 120° C. in an oil bath for 5 hours, volatiles were removed from the reaction mixture under high vacuum overnight. The resulting brown residue was diluted in ethyl acetate (60 mL) and washed with water (2×25 mL) and brine (1×25 mL). The organic fraction was dried over anhydrous $Na_2SO_4$, filtered and concentrated in vacuo. Purification by column chromatography on silica gel (1:1 hexanes/ethyl acetate) yielded 141 mg (41%) of the desired product. $^1$H NMR (400 MHz, CDCl$_3$) δ: 8.07 (br s, 1H) 7.65 (d, J=16 Hz, 1H), 7.43 (s, 1H), 7.40 (d, J=8.2 Hz, 1H), 6.89 (d, J=8.0 Hz, 1H), 6.34 (d, J=16 Hz, 1H), 3.80 (s, 3H), 3.57 (s, 2H). ESI-MS 240 (M+Na)$^+$, 457 (2M+Na)$^+$

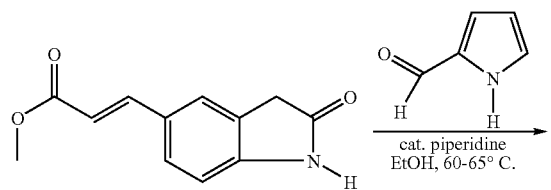

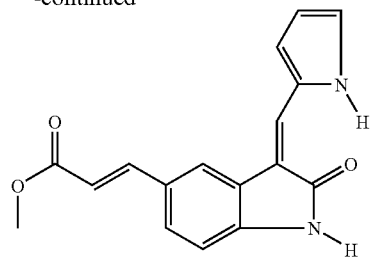

To a solution of the enoateoxindole prepared as above (21 mg, 0.097 mmol) in 1 mL EtOH was added pyrrole 2-carboxaldehyde (15 mg, 0.158 mmol) and piperidine (0.8 μL, 0.008 mmol). The orange mixture was heated and kept at 65° C. for 15 hours. The precipitated product was filtered to separate it from unreacted pyrrole 2-carboxaldehyde. The retentate was washed with cold ethanol (3×2 mL) and dried in a vacuum desiccator to yield 11 mg (39%) of the desired compound. $^1$H NMR (400 MHz, DMSO-d6) δ: 13.26 (br s, 1H), 11.13 (br s, 1H), 8.16 (s, 1H), 7.90 (s, 1H), 7.65 (d, J=16 Hz, 1H), 7.47 (dd, J=8.2 Hz, 1.5 Hz, 1H), 7.47 (m, 1H), 6.91 (d, J=8 Hz, 1H), 6.84 (m, 1H), 6.60 (d, J=15.9 Hz, 1H), 6.39 (m, 1H), 3.73 (s, 3H). ESI-MS 317 (M+Na)$^+$

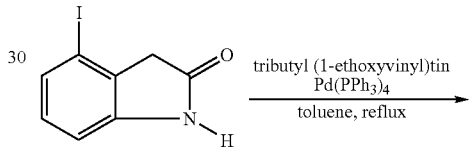

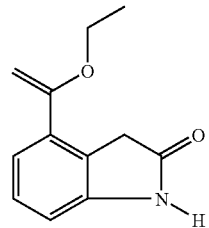

Figure 2:
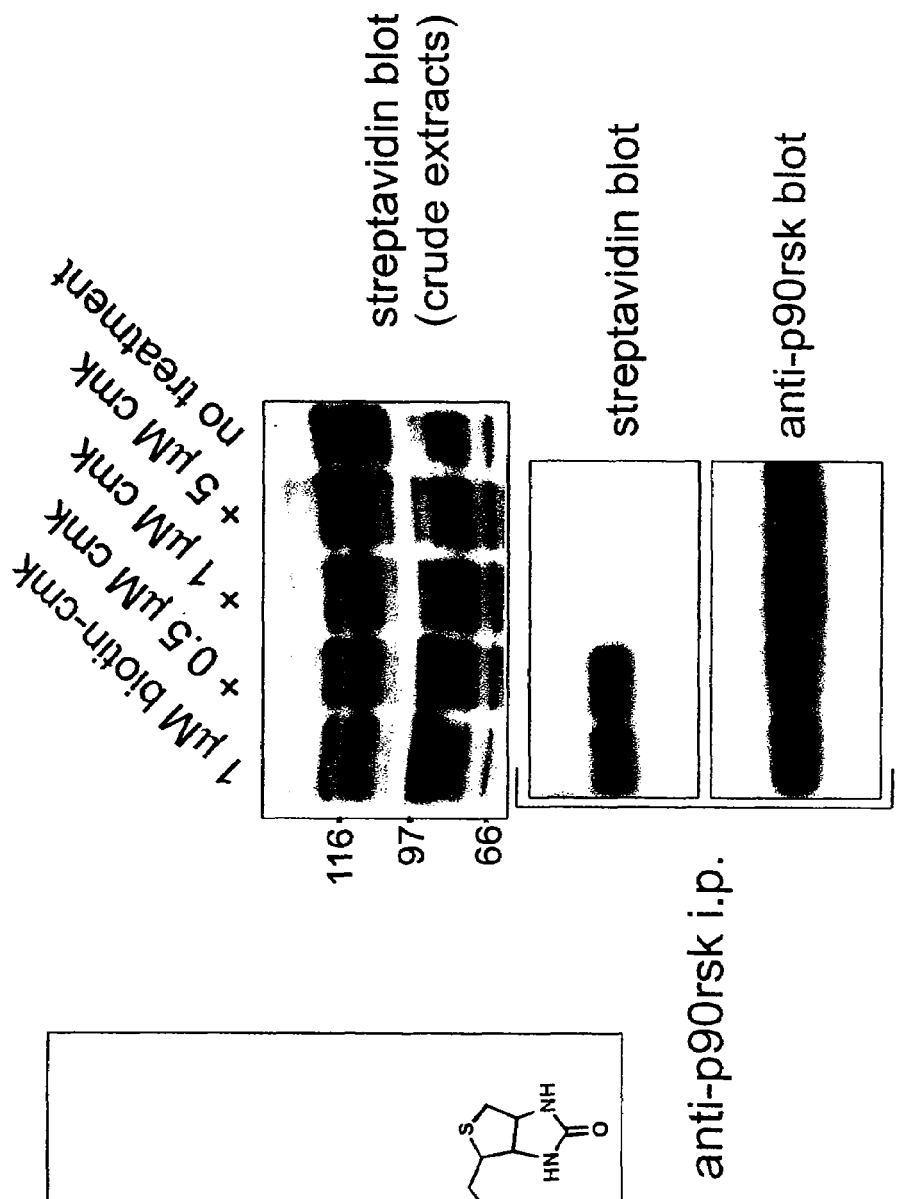
FIG. 2 depicts specific labeling of Rsk2 by biotinylated 1 in *Xenopus* egg extracts.

To a solution of 4-iodooxindole (296 mg, 1.14 mmol) in 10 mL dry toluene at room temperature was added tributyl(1-ethoxyvinyl)tin (480 μl, 1.42 mmol) and tetrakistriphenylphosphine palladium (158 mg, 0.137 mmol) under an Ar atmosphere. The brown mixture was heated to reflux for 10 hours. Volatiles were removed by evaporation in vacuo and the resulting residue dissolved in ethyl acetate (50 mL), washed with water (3×25 mL) and brine (2×25 mL). The organic fraction was dried over anhydrous $Na_2SO_4$, filtered and concentrated in vacuo. Purification by column chromatography on silica gel (1:1 hexanes/ethyl acetate) yielded 81 mg (35%) of the desired compound. $^1$H NMR (400 MHz, CDCl$_3$) δ: 8.98 (br s, 1H) 7.20 (m, 2H), 6.85 (d, J=5.7 Hz, 1H), 4.53 (d, J=2.5 Hz, 1H), 4.29 (d, J=2.6 Hz, 1H), 3.90 (q, J=7 Hz, 2H), 3.70 (s, 2H), 1.42 (t, J=7 Hz, 3H). ESI-MS 226 (M+Na)$^+$, 429 (2M+Na)$^+$ Tests of Compounds as Kinase Inhibitors To test whether compounds 1 and 2 (Formula IA, chloromethyl ketone and methyl enoate respectively) bind selectively and irreversibly to Rsk2, compound 1 was labeled with biotin. *Xenopus* egg cytosol was treated with 1 μM biotin-1. A major biotinylated 90 kD protein was detected by immunoblot analysis with streptavidin-HRP. Labeling of p90 with biotin-1 was abolished by pretreatment of the cytosol 1 μM of unlabeled 1. Thus, p90 is completely saturated by 1 at a concentration of 1 µM. Immunoprecipitation of Rsk2 with a monoclonal antibody (Santa Cruz Biotech) followed by immunoblot analysis with streptavidin-HRP demonstrated unequivocally that biotin-1 irreversibly targets Rsk2 in *Xenopus* egg cytosol, and that binding is saturable by 1 µM of 1 (FIG. 2)

Because streptavidin-HRP detection resulted in a high background, even in untreated cytosol, we prepared bodipy-1, which contains the green fluorophore FL-bodipy (Molecular Probes). Bodipy-1 labeled a single major protein of 90 kD as detected by a confocal laser gel scanner (Amersham). Labeling was abolished by pretreatment with 1 µM of 1 or 2. Labeling of minor bands by bodipy-1 was not prevented by 1 or 2, suggesting that these proteins are nonspecifically targeted by bodipy-1.

Figure 4:
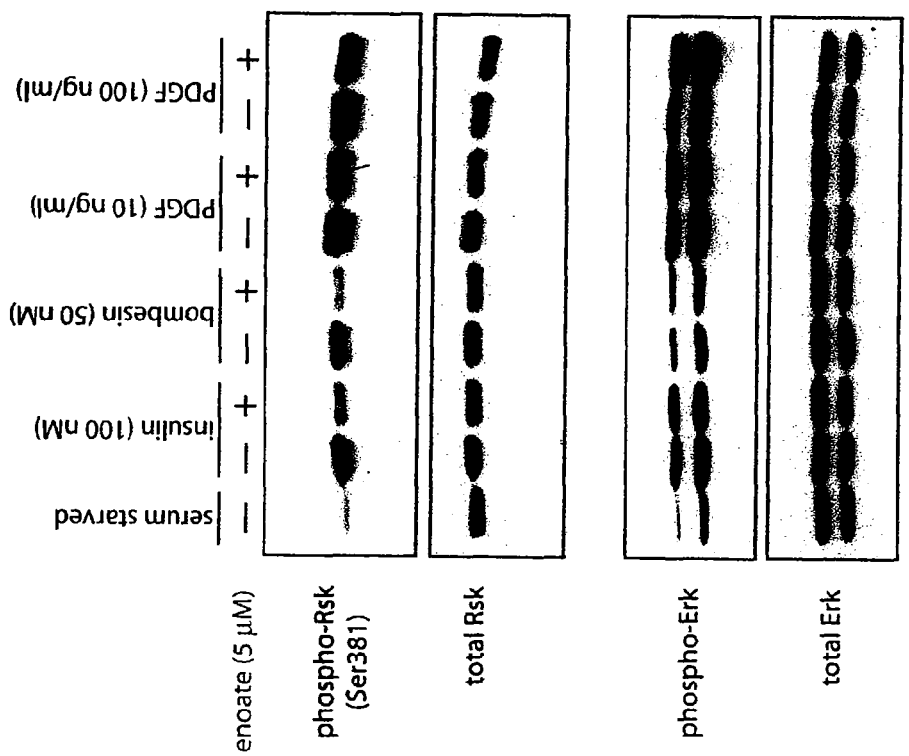
FIG. 4 shows inhibition by the enoate of Rsk autophosphorylation in Swiss 3T3 fibroblasts.

Enoate 2 blocks Rsk autophosphorylation of Ser381, which is catalyzed by its cysteine-containing C-terminal kinase domain. The enoate does not block Erk phosphorylation. Swiss 3T3 cells were serum starved for 24 hours and treated with 5 µM enoate or 0.1% DMSO (control) for 1 hour. The cells were then stimulated with growth factors for 10 min. and lysed with 1×SDS-PAGE sample buffer. Proteins were separated by SDS-PAGE and transferred to nitrocellulose membranes for Western blot analysis. Phosphorylation-specific antibodies against Rsk and Erk were purchased from Cell Signaling. Antibodies against nonphosphorylated Rsk and Erk were purchased from Santa Cruz Biotech and Cell Signaling, respectively. (FIG. 4.)

Time-Dependent Inhibition of V282C Fyn Kinase Activity In Vitro.

Figure 6:
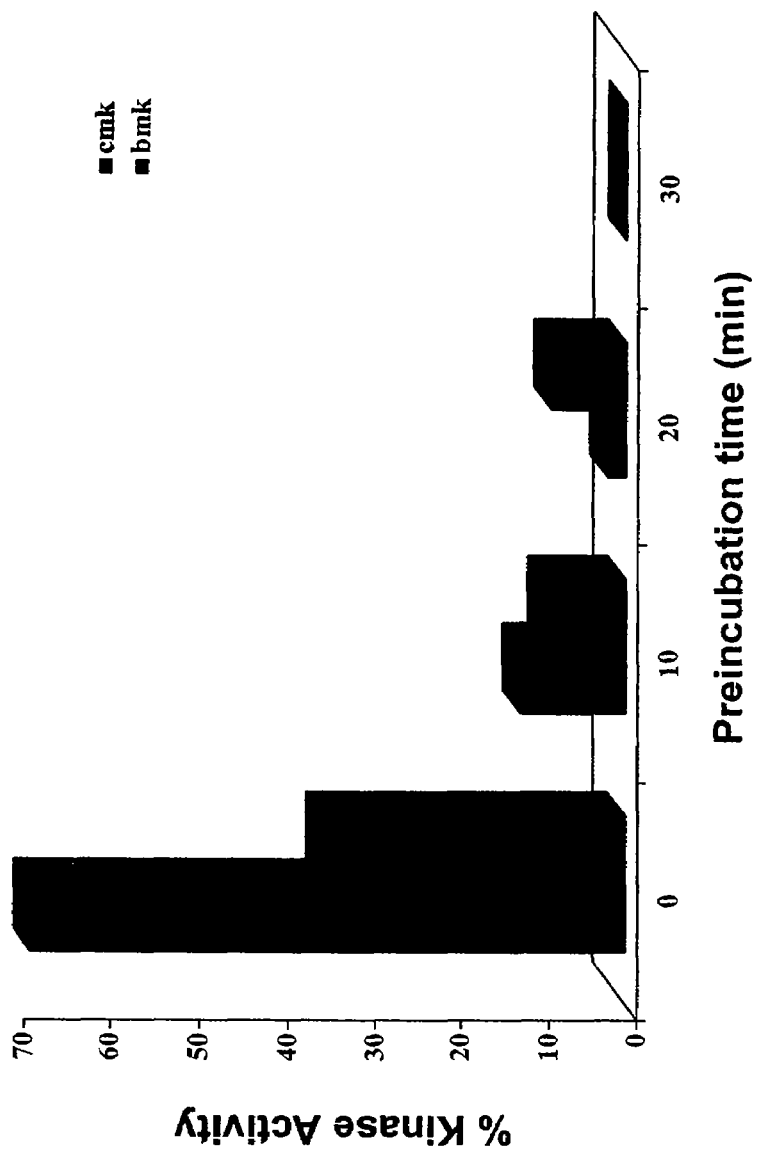
FIG. 6 is a graphical depiction of data from an experiment in which V282C Fyn was incubated with 10 nM bmk 3 or cmk 4 for varying times.

Halomethylketones 3-5 (FIG. 5) were screened against the catalytic domain of wt Fyn and V282C Fyn, which were bacterially expressed and purified as a glutathione-S-transferase (GST) fusion proteins. All three compounds exhibited time-dependent inactivation of V282C Fyn kinase activity. At a concentration of 10 nM cmk 3 or bmk 4, complete inactivation was achieved within 30 min (see FIG. 6), whereas inactivation by fmk 5 was much slower (data not shown). Significantly, 3-5 do not affect the kinase activity of wt Fyn at concentrations required to inhibit 90% of the activity of V282C Fyn. These data are consistent with the notion that compounds 3-5 selectively inactivate V282C Fyn via covalent modification of the engineered cysteine residue.

Covalent Labeling and Selective Inhibition of v-Src-es1 in Mammalian Cells.

To test whether cmk 4 could covalently label and inhibit Src kinases in vivo, we generated NIH3T3 fibroblast cell lines that stably overexpress either a wt v-Src allele or an electrophile-sensitive mutant, V281C v-Src (v-Src-es1). v-Src is constitutively active, and as a result of its expression in these cells, there is a substantial increase in phosphotyrosine levels. Because Src and Fyn are 85% identical in their kinase domains, we expected that an active site cysteine mutant of v-Src would be sensitive to cmk 4 with similar potency to that observed for V282C Fyn. To test whether cmk 4 forms an irreversible, covalent bond with V281C v-Src, we conjugated biotin to the hydroxypropyl substituent. This point of attachment was chosen based on the model of cmk 4 bound to Hck in which the hydroxypropyl substituent is pointing out into solution.

NIH3T3 fibroblasts expressing either v-Src-es1 or v-Src were pretreated with increasing concentrations of cmk 4. Whole cells lysates were then prepared and treated with biotin-cmk (2 µM). Immunoprecipitation of v-Src with a monoclonal antibody followed by immunoblot analysis with streptavidin (horseradish peroxidase conjugate) demonstrated that biotin-cmk covalently targeted v-Src-es1. Labeling of v-Src-es1 was abolished by pretreatment of intact cells with 1 µM cmk 4 ($IC_{50}$<100 nM). The absence of covalent labeling observed for wt v-Src demonstrates that the engineered cysteine is required for modification by cmk 4.

Figure 7:
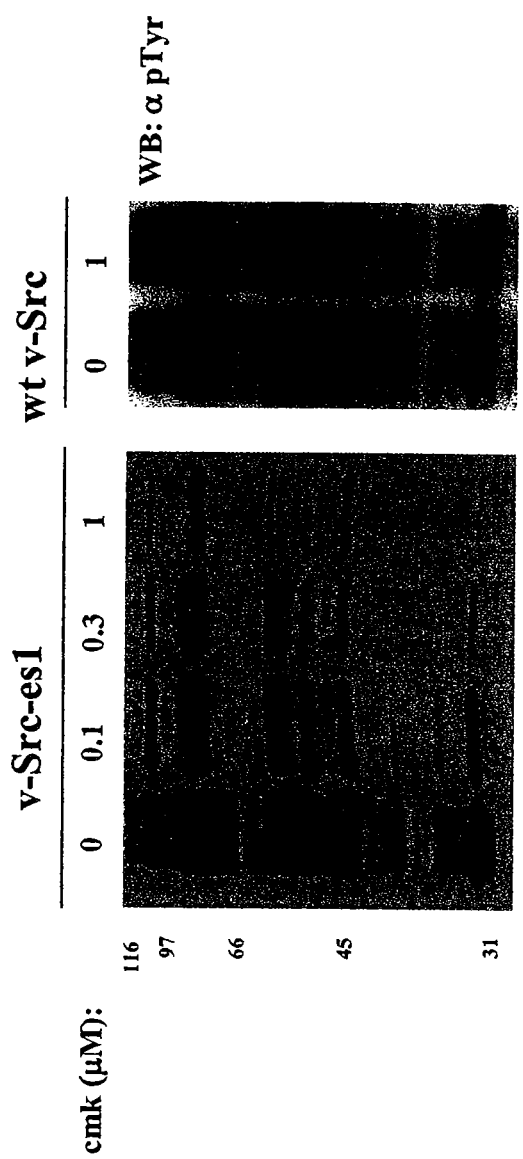
FIG. 7 depicts results from an experiment testing inhibition of tyrosine phosphorylation by cmk 4 in NIH-3T3 cells expressing V281C-v-Src (v-Src-es1) or wild-type v-Src.

We also investigated whether cmk 4 could block the function of v-Src-es1 in mammalian cells by monitoring global phosphotyrosine levels in cells expressing either wt v-Src or v-Src-es1. Cells overexpressing v-Src-es1 showed a dose-dependent decrease in tyrosine phosphorylation upon treatment with cmk 4 (FIG. 7), with a near-complete reduction of detectable phosphotyrosine at a concentration of 1 µM. In contrast, cmk 4 at 1 µM had no apparent effect on cells overexpressing wt v-Src. These data are consistent with the labeling experiments and indicate that the specificity of cmk 4 for v-Src-es1 is due to the selective covalent modification of a single cysteine within the active site of the kinase.

Reversion of Transformed Morphology in Cells Expressing v-Src-es1.

Figure 8:
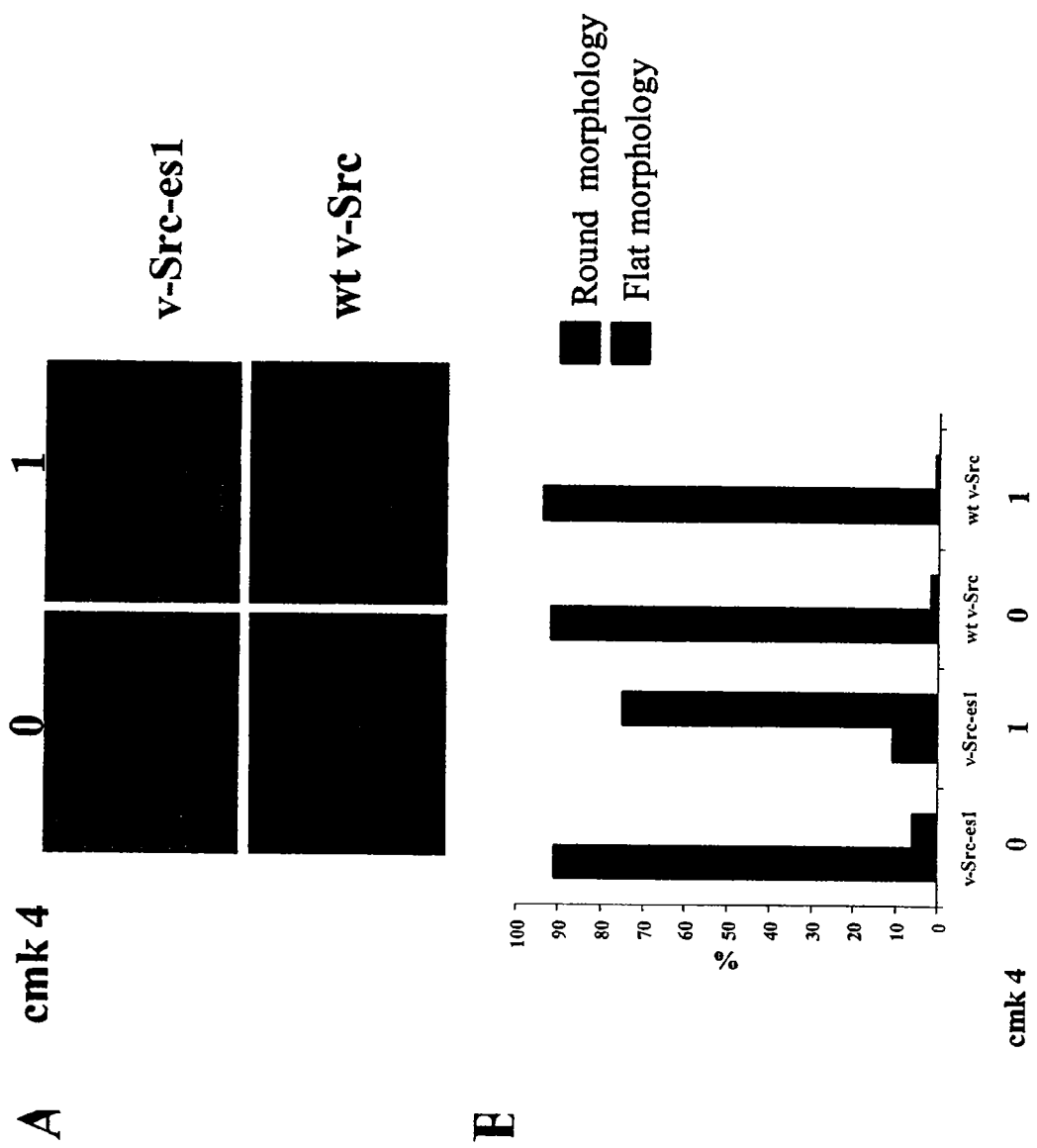
FIG. 8 shows that cmk 4 causes morphological detransformation of V281C-v-Src-expressing fibroblasts.

Overexpression of v-Src in NIH3T3 fibroblasts causes morphological transformation. Nontransformed NIH3T3 cells have a flat morphology, characterized by long bundles of filamentous actin ("stress fibers") that can be visualized by fluorescence microscopy. In contrast, NIH3T3 cells overexpressing wt v-Src or v-Src-es1 have a disorganized actin cytoskeleton that results in a round morphology. Treatment of cells expressing v-Src-es1 with cmk 4 (1 µM) for 16 h caused reversion of the transformed morphology as evidenced by the appearance of actin stress fibers after fixing the cells and staining filamentous actin with FITC-phallodin (FIG. 8A). Under the same conditions, cells expressing wt v-Src are not affected by cmk 4 and maintain a round morphology (FIG. 8A). The effects of cmk 4 on cell morphology were quantified by counting 100-200 cells under each treatment condition for both wt v-Src and v-Src-es1. Approximately 80% of the cells expressing v-Src-es1 regain a flattened morphology upon treatment with 1 µM cmk 4, whereas less than 2% of cells expressing wt v-Src have actin stress fibers (FIG. 8B). These data show that treatment of cells expressing v-Src-es1 with 1 µM cmk 4 is sufficient to block the ability of v-Src to cause morphological transformation.

Tests of Fluoromethyl Ketone (fmk), Compound 5

We tested the halomethylketones against the Rsk2 CTD by adapting an in vitro kinase assay developed by Chrestensen and Sturgill, *J, Biol. Chem.* 277:27733 (2002). Both cmk 4 (not shown) and fmk 5 (Table 1 below) potently inhibited the kinase activity of Rsk2 CTD. The fmk 5 has greater chemical stability. Fmk 5 (1 µM) exhibited time-dependent inactivation of Rsk2 CTD, with a half-time of less than 10 min in the presence of 1 mM ATP. Inhibition of wild-type Rsk2 CTD was found to be accompanied by irreversible covalent bond formation. Erk2, which is required to activate Rsk2 CTD in vivo and in vitro, was not labeled by biotinylated fmk 5, despite the presence of a solvent-exposed cysteine in its ATP binding pocket.

TABLE 1

| | $IC_{50}$ values, µM | | |
|---|---|---|---|
| | WT | C436V | T439M |
| fmk 5 | 0.015 ± 0.001 | >10 | 3.4 ± 0.3 |
| scaffold A (no electrophile; hydroxyl group not protected) | 1.2 ± 0.08 | 0.43 ± 0.14 | >30 |

Similarly, enone 15 and propargylamine-fmk 18 were shown to inhibit RSK2 with IC50 less than 1 μM To test whether both Rsk2 selectivity filters, namely Cys436 and Thr493, are required for inhibition by fmk 5, we expressed and purified two CTD mutants, Cys436Val and Thr493Met, whose kinase activities are essentially identical to that of the wild-type protein. The Cys436Val mutant still contains a cysteine (Cys560) in the ATP binding pocket which, based on other kinase structures, is predicted to be 8-9 Å from Cys436. Consistent with our dual selectivity filter hypothesis, both mutants were resistant to inhibition and covalent modification by fmk 5 (Table 1). Fmk 5 is remarkably potent against the WT kinase (IC50=15 nM in the presence of 0.1 mM ATP, 30 min pretreatment), with greater than 600- and 200-fold selectivity over the Cys436Val and Thr493Met mutants, respectively (Table 1). The electrophilic fluoromethylketone group is required for potent inhibition, as the parent scaffold (FIGS. 5, 1) is 80-fold weaker than fmk 5 toward WT Rsk2 (Table 1). In contrast, scaffold 3 is much more potent than fmk 5 against the Cys436Val mutant. Together, these results strongly support the notion that fmk 5 inhibits Rsk2 via (i) covalent modification of Cys436, and (ii) insertion of the C-5 aromatic substituent into a hydrophobic pocket defined by the gatekeeper, Thr493. To our knowledge, fmk 5 is the first reported inhibitor of a Rsk-family CTD.

The only known Rsk2 CTD substrate is an autophosphorylation site, Ser386, in the linker region connecting the NTD and CTD. Phosphorylation of Ser386 creates a docking site for another kinase, phosphoinositide-dependent kinase 1 (PDK1), which phosphorylates and activates the NTD. To test whether fmk 5 inhibits Rsk2 CTD activity in mammalian cells, we monitored phospho-Ser386 levels with a phosphorylation-specific antibody. Treatment of serum-starved COS-7 cells with EGF led to a dramatic increase in Ser386 phosphorylation, which was blocked by fmk 5 with an IC50 of ~200 nM. At 3 μM fmk 5, Ser386 phosphorylation was reduced by 95%. These data strongly support the notion that the CTD is the primary kinase responsible for EGF-stimulated Ser386 phosphorylation. As a further specificity test, we asked whether fmk 5 blocked activation of Erk1/2, the MAP kinases directly upstream of Rsk2. The signaling pathway between EGF and Erk1/2 involves at least three protein kinases (EGFR, Raf, and MEK), two of which (EGFR and Raf) have threonine gatekeepers and cysteines in their ATP binding pockets (albeit at different locations relative to Rsk2 Cys436). Fmk 5 (at 10 μM) had no effect on EGF-stimulated phosphorylation of the key Erk1/2 regulatory sites, Thr202 and Tyr204. Thus, fmk 5 inhibits Rsk2 CTD activity in mammalian cells, but does not block signaling between EGF and Erk1/2.

A major concern with any pharmacological agent is its selectivity, not only among related family members, but among all other coexpressed proteins. To determine the global kinetic selectivity of fmk 5, we added a biotinylated derivative to a crude lysate prepared from human epithelial cells. Only two proteins in the lysate were labeled. These ~90 kD biotinylated proteins were shown to be Rsk1/2 by quantitative immunodepletion with specific antibodies. Affinity purified antibodies raised against a Rsk1 peptide specifically immunoprecipitated the lower band, whereas a Rsk2 monoclonal antibody was specific for the upper band. Both proteins remained in the supernatant when a control rabbit IgG was used. Covalent labeling of Rsk1/2 was suppressed by pretreatment with unlabeled fmk 5, and complete saturation was observed at 0.3 μM and 1 μM for Rsk1 and Rsk2, respectively. Thus, fmk 5 appears to be one of the most specific irreversible inhibitors known, as it reacts preferentially with Rsk1/2 in cell lysates containing thousands of potentially reactive proteins.

Cmk 4 and fmk 5 also were tested against the Src-family kinase Fyn, which has a threonine gatekeeper, which in principle should recognize the C-5 aromatic substituent of our inhibitors. At a concentration of 30 nM, cmk 4 had no effect on wild-type (WT) Fyn, whereas it rapidly inactivated an engineered Fyn construct containing a cysteine in place of Val285. In the presence of 1 mM ATP, WT Fyn was relatively resistant to both cmk 4 and fmk 5, with IC50 values of 18 and 24 mM, respectively. In contrast, 100 nM cmk 4 inactivated Val285Cys Fyn in less than 5 min under these conditions. Cmk 4 was 100-fold more potent than fmk 5 toward Val285Cys Fyn.

Click Chemistry.

Click reactions were performed as previously described by Speers et al., "Profiling enzyme activities in vivo using click chemistry methods". *Chem Biol* 11, 535-46 (2004). Briefly, RSK2 CTD (30 nM) pretreated with the indicated concentrations of fmk-pa, or lysates from fmk-pa-pretreated cells were incubated with TAMRA-N3 or biotin-N3 (50 mM), TCEP (1 mM), $CuSO_4$ (1 mM), and TBAT (100 mM) in PBS [pH 7.4] containing 1% SDS for 1 h at room temperature. Proteins were resolved by 10% SDS-PAGE and detected by in-gel fluorescence scanning (TAMRA-N3) or were affinity purified with avidin-agarose and detected by Western blotting (biotin-N3).

PMA-stimulated RSK Ser386 and rpS6 Ser235/236 phosphorylation in HEK-293 cells.

Confluent HEK-293 cells in 12-well plates were deprived of serum for 2 h and subsequently treated with the indicated concentrations of inhibitors for 1 h at 37° C. After stimulation with PMA (0.1 mg/mL) for 30 min, cells were washed with cold PBS and harvested in either PBS lysis buffer (FIG. 9c) or hypertonic lysis buffer (FIG. 10). Click chemistry was performed with TAMRA-N3 in lysates from cells treated with fmk-pa. Proteins were analyzed by in-gel fluorescence scanning or Western blotting.

Figure 9:
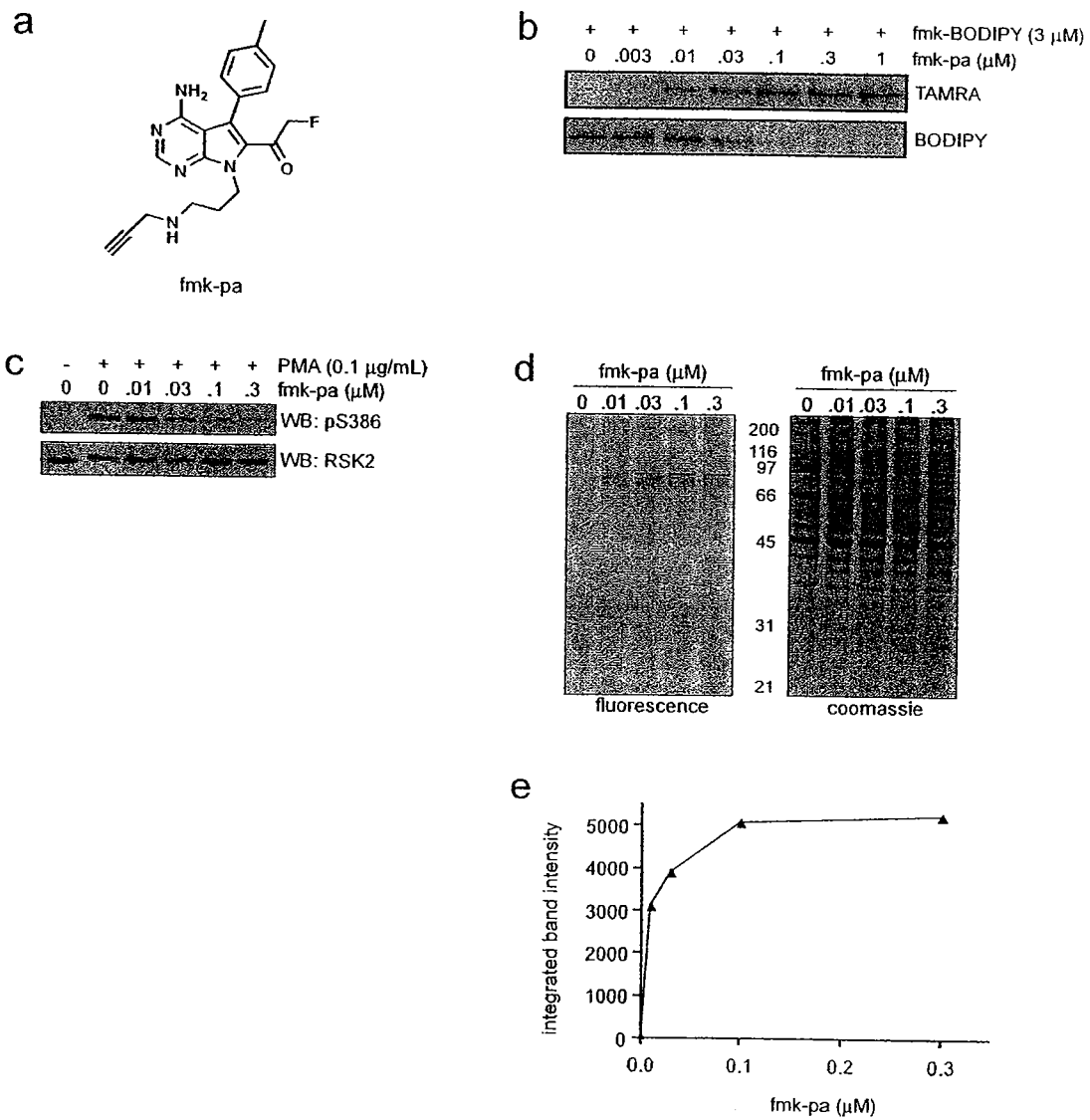
FIG. 9 depicts inhibition of RSK by fmk-pa.
Figure 10:
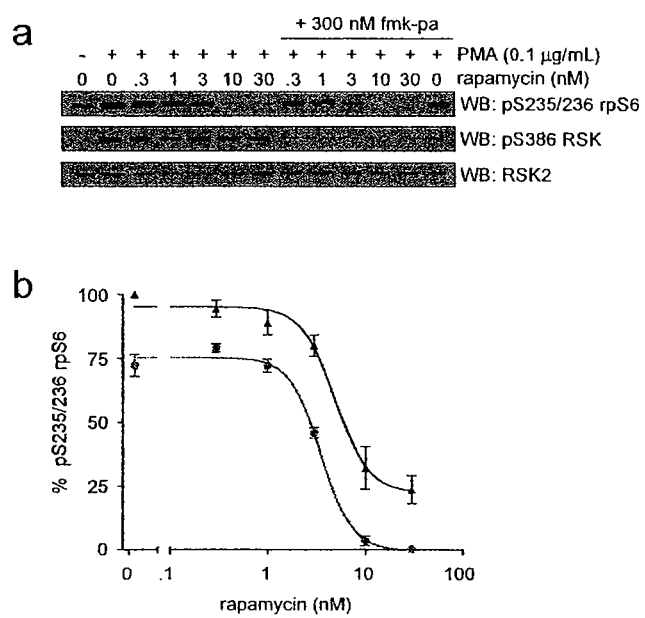
FIG. 10 shows that fmk-pa reveals a RSK CTD-dependent pathway for rpS6 phosphorylation.

FIG. 9 depicts the irreversible, selective, and potent inhibition of RSK by fmk-pa. FIG. 9(a) shows the chemical structure of fmk-pa, a clickable propargylamine variant of fmk. FIG. 9(b) shows click chemistry-mediated detection of RSK2 CTD. RSK2 CTD was treated with the indicated concentrations of fmk-pa for 1 h followed by 3 mM fmk-BODIPY for 1 h. After click conjugation with TAMRA-N3 (see Methods), proteins were resolved by 10% SDS-PAGE and detected by sequential in-gel fluorescence scanning using filters specific for TAMRA and BODIPY. FIG. 9(c) depicts the effect of fmk-pa on PMA-stimulated Ser386 RSK phosphorylation. HEK-293 cells were deprived of serum for 2 h and subsequently treated with the indicated concentrations of fmk-pa for 1 h. Cells were stimulated with PMA (100 ng/mL) for 30 min and processed to resolve proteins by 10% SDS-PAGE. FIG. 9(d) depicts selectivity of protein modification by fmk-pa in intact cells. Cell lysates from 9(c) were subjected to click conjugation with TAMRA-N3. Proteins were resolved by 10% SDS-PAGE and detected by in-gel fluorescence scanning (left) and Coomassie blue staining (right). FIG. 9(e) shows the quantification of fluorescent bands in 9(d).

Figure 3:
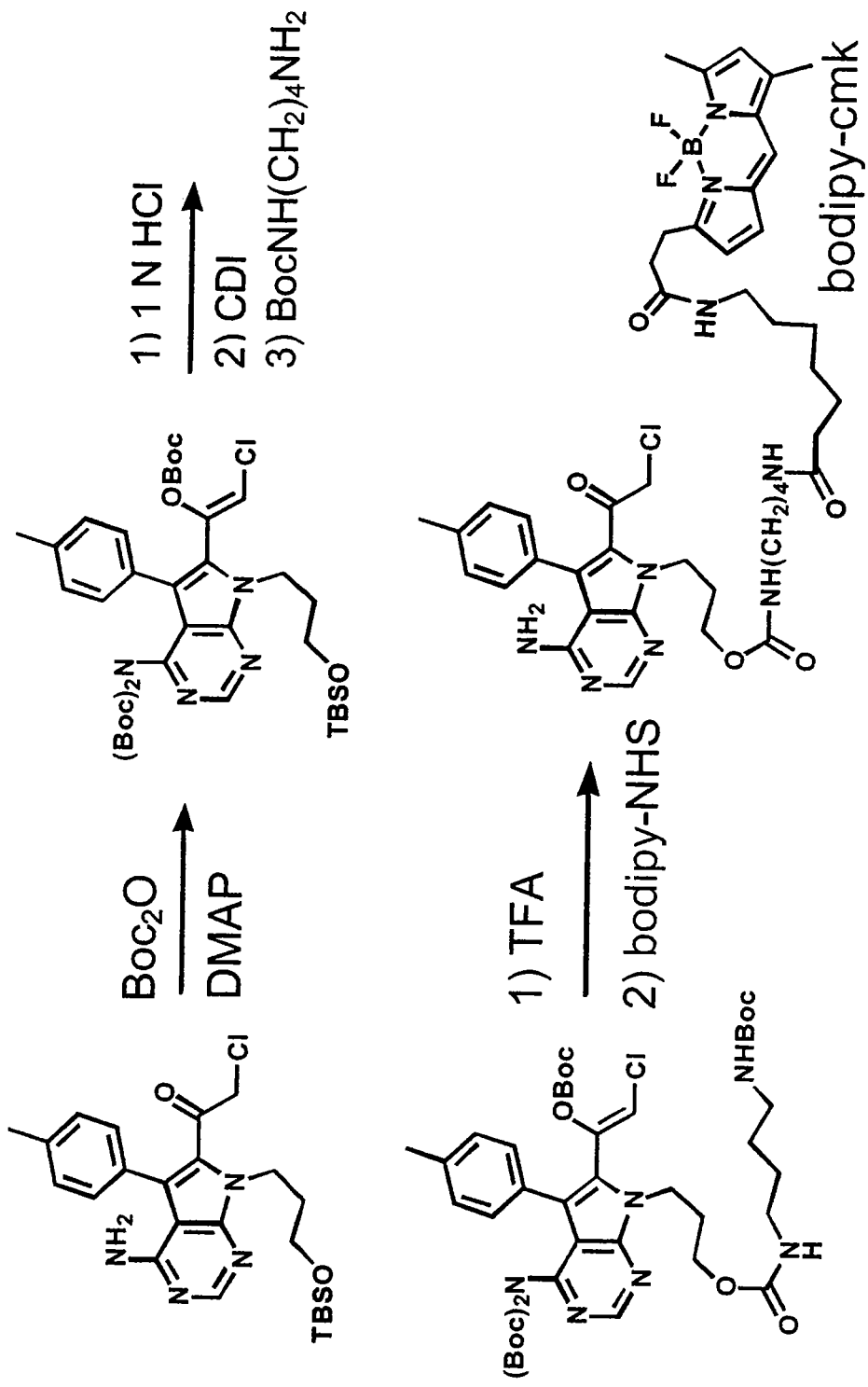
FIG. 3 shows a synthesis scheme for bodipy-cmk. The same procedure was used to prepare biotinylated-cmk using biotin-NHS ester.

Fmk-pa reveals a RSK CTD-dependent pathway for rpS6 phosphorylation. FIG. 10(a) shows the effects of rapamycin and fmk-pa on rpS6 phosphorylation. Serum-starved HEK-293 cells were treated with the indicated concentrations of rapamycin in the absence (left lanes) or presence (right lanes) of 300 nM fmk-pa for 1 h and stimulated with PMA (100 ng/mL) for 30 min. Proteins were resolved by 10% SDS-PAGE and detected by Western blotting with antibodies to phospho-Ser235/236 rpS6, phospho-Ser386 RSK, and total RSK2. FIG. 10(b) shows dose-response curves showing additive inhibition of rpS6 phosphorylation: rapamycin alone (black triangles) and rapamycin+300 nM fmk-pa (gray circles). Percent rpS6 Ser235/236 phosphorylation was determined by quantification of Western blots (e.g., FIG. 3a) relative to DMSO controls using ImageJ. Data represent mean±s.e.m. from 3 independent experiments.

LPS and PMA Stimulation of Primary Mouse Macrophages.

Confluent macrophages in 12-well plates were incubated in DMEM supplemented with 20 mM Hepes [pH 7.4] and 0.5% FBS for 12 h prior to treatment with the indicated concentrations of fmk-pa for 1 h at 37° C. After stimulation with either PMA (0.1 mg/mL) or LPS (1 mg/mL) for 30 min, cells were washed with cold PBS and harvested in PBS lysis buffer. Click chemistry was performed with TAMRA-N3 and proteins were subsequently analyzed by in-gel fluorescence scanning or Western blotting.

Figure 11:
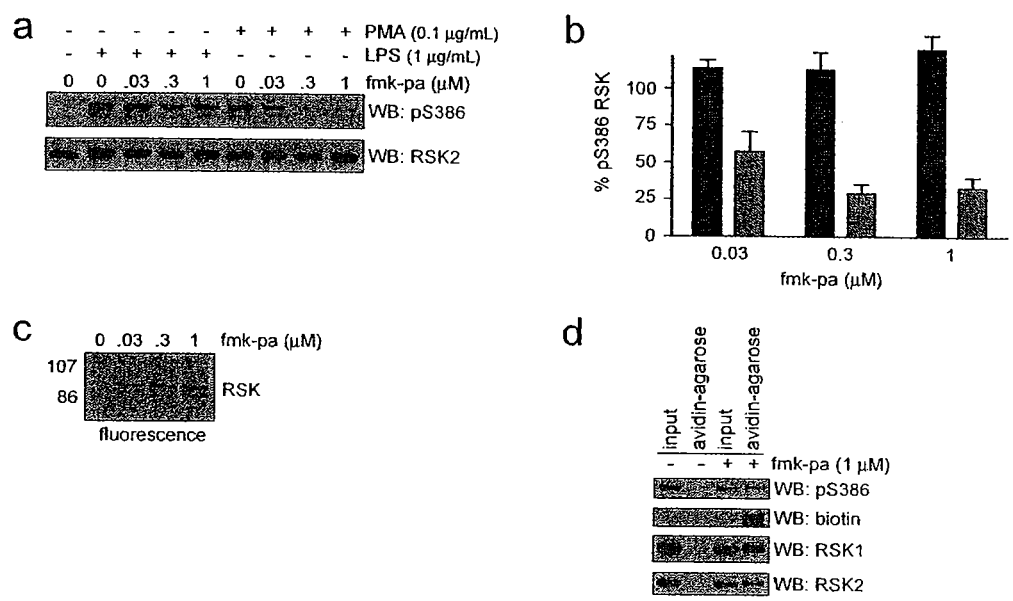
FIG. 11 shows that fmk-pa and click chemistry reveal the existence of a CTD-independent pathway for RSK Ser386 phosphorylation.

FIG. 11. Fmk-pa and click chemistry reveal the existence of a CTD-independent pathway for RSK Ser386 phosphorylation. FIG. 11(a) shows the effect of fmk-pa on Ser386 phosphorylation in primary bone marrow-derived macrophages stimulated with lipopolysaccharide (LPS) and PMA. Macrophages were cultured in 0.5% serum for 20 h and subsequently treated with the indicated concentrations of fmk-pa for 1 h. Cells were stimulated with either PMA (100 ng/mL) or LPS (1 mg/mL) for 30 min and harvested in PBS. Proteins were resolved by 10% SDS-PAGE and detected by Western blotting with antibodies to phospho-Ser386 RSK and total RSK2. FIG. 11(b) shows the determination of Percent Ser386 phosphorylation by quantification of Western blots (e.g., FIG. 11a) relative to DMSO controls. Data represent mean±s.e.m. from 3 independent experiments. FIG. 11(c) shows saturable RSK modification by pretreatment of intact macrophages with fmk-pa. Lysates from LPS-stimulated macrophages (pretreated for 1 h with the indicated concentrations of fmk-pa) were incubated with TAMRA-N3 under the click reaction conditions. Proteins were resolved by 10% SDS-PAGE and detected by in-gel fluorescence scanning. FIG. 11(d) illustrates the use of click chemistry to demonstrate that RSK1/RSK2 modified by fmk-pa are phosphorylated at Ser386 in response to LPS stimulation. Lysates from LPS-stimulated cells (pretreated with 1 mM fmk-pa or DMSO control) were incubated with biotin-N3 under the click reaction conditions for 1 h. Biotinylated proteins were affinity purified with avidin-agarose beads. Eluted proteins were resolved by 10% SDS-PAGE and detected by Western blotting with streptavidin-HRP or antibodies to RSK1, RSK2, and phospho-Ser386 RSK.

Avidin Pulldown from LPS-Stimulated Primary Macrophages.

Confluent primary macrophages in 15 cm plates were incubated in DMEM supplemented with 20 mM Hepes [pH 7.4] and 0.5% FBS for 12 h prior to treatment with either DMSO or 1 mM fmk-pa for 1 h at 37° C. Lysates (200 mL, 5 mg/mL) prepared in PBS were subjected to click chemistry to conjugate biotin-N3 to fmk-pa-modified RSK. After the click reaction, proteins were precipitated using 15% (v/v) trichloroacetic acid (TCA) and pelleted by centrifugation (13,000 rpm, 5 min, 4° C.). The supernatant was removed and the protein pellet was washed twice with ice-cold acetone (2×200 mL). The resulting acetone pellet was solubilized in PBS (40 mL) containing 2% (w/v) SDS by heating and sonication. Samples were diluted 10-fold in PBS containing 0.5% (v/v) NP40 (400 mL, 0.9 mg/mL).

Avidin-agarose (30 mL of 50% slurry in PBS) was added and samples were rotated overnight at 4° C. The post-avidin supernatant was removed and the beads were washed with PBS containing 0.5% NP40 and 0.1% SDS (2×1 mL). Affinity purified proteins were eluted from the beads with 2× Laemmli sample buffer containing 1 mM biotin (100 mL), resolved by 10% SDS-PAGE, and detected by Western blotting.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A compound having the formula (IA):

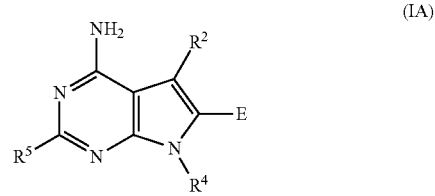

in which
R$^2$ is hydrogen or a group having the formula —(CH$_2$)$_b$R$^b$ wherein b is 0 or an integer from 1 to 3 and R$^b$ is an aromatic, heterocyclic or cyclical aliphatic group optionally substituted with one or more groups selected from lower alkyl, halogen, substituted alkyl, nitro, alkoxy, phenoxy, sulfonamido, carboxylic ester, a fluorescent label, an affinity tag, or carboxamide;

R$^4$ is an aliphatic, aromatic, or heterocyclic group optionally substituted with a fluorescent label, an affinity tag, or one or more polar groups, which polar group may be protected or unprotected;

R$^5$ is hydrogen, a fluorescent label, an affinity tag, or an alkyl- or aryl-substituted ether, thioether, or amine; and E is —(CH$_2$)$_m$COR', —CO(CH$_2$)$_n$R', —C(O)C(O)R', or an olefin attached to an electron withdrawing group, wherein m and n are independently 0 or an integer from 1 to 6, wherein R' is independently halogen, cyano, alkyl, substituted alkyl, aryl, substituted aryl, heterocyclic group or substituted heterocyclic group, and wherein the substituted alkyl, substituted aryl and substituted heterocyclic group are independently substituted with halo, hydroxyl, thiol, nitro, amino, amido, alkoxy, haloalkoxy, alkylenedioxy, alkyl, haloalkyl, or hydroxyalkyl.

2. A compound according to claim 1 in which R$^2$ is hydrogen.

3. A compound according to claim 1 in which R$^2$ is a group having the formula (CH$_2$)$_b$R$^b$.

4. A compound according to claim 3 in which b is 0.

5. A compound according to claim 4 in which R$^2$ is an optionally substituted phenyl group.

6. A compound according to claim 5 in which R$^2$ is a p-tolyl group.

7. A compound according to claim 1 in which E is an olefin attached to nitro or cyano.

8. A compound according to claim 7 in which E is an olefin attached to a cyano.

9. A compound according to claim 1 in which E is —C(O)(CH$_2$)$_n$R' in which R' is a halogen and n is 0 or an integer from 1 to 6.

10. A compound according to claim 9 in which n is 0.

11. A compound according to claim 9 in which n is 1.

12. A compound according to claim 1 in which E is —(CH$_2$)$_m$C(O)R' in which m is 0 or an integer from 1 to 6 and R' is a halogen.

13. A compound according to claim 12 in which m is 0.

14. A compound according to claim 12 in which m is 1.

15. A compound according to one of claim 9 or 12 in which R' is chloro.

16. A compound according to one of claim 9 or 12 in which R' is fluoro.

17. A compound according to claim 1 in which E is —C(O)CH=CH$_2$.

18. A compound according to claim 1 in which E is —CH=CH—C(O)CH$_3$.

19. A compound according to claim 1 in which E is —CH=CHC(O)OR' where R' is an optionally substituted aliphatic, aromatic, or heterocyclic moiety.

20. A compound according to claim 19 in which R' is methyl.

21. A compound according to claim 1 in which R$^4$ is an aliphatic substituted with an amino or substituted amino group and E is a halomethyl ketone.

22. A compound according to claim 1 in which R$^4$ is an optionally substituted phenyl amino group.

23. A compound according to claim 1 in which R$^4$ is an optionally substituted lower aliphatic amino group.

24. A compound according to claim 1 in which R$^4$ is an optionally substituted lower alkynyl amino group.

25. A compound according to claim 1 in which R$^4$ is a propargylamino group.

26. A therapeutic composition comprising (a) a kinase inhibitory-effective amount of a composition according to claim 1 and a pharmaceutically acceptable carrier.

27. A composition for inhibiting kinase activity comprising an effective inhibitory amount of a compound according to claim 1.

28. A composition according to claim 27 for inhibiting activity of a kinase selected from the group consisting of Rsk1,2,3,4, Msk1-2, Plk1-3, MEKK1, and Nek.

29. A compound according to claim 1 in which R$^5$ is hydrogen.

30. A compound according to claim 1 in which is R$^4$ an aliphatic, aromatic, or heterocyclic group substituted with a fluorescent label or an affinity tag.

31. A compound according to claim 30 in which

R$^5$ is hydrogen; and

E is —CH=CH—C(O)—OCH$_3$ or —CO(CH$_2$)$_n$R', wherein n is 1 and R' is chloro or fluoro.

32. A compound according to claim 30 in which

R$^5$ is hydrogen; and

E is —CO(CH$_2$)$_n$R', wherein n is 1 and R' is chloro or fluoro.

33. A compound according to claim 1 in which

R$^2$ is hydrogen or a group having the formula —(CH$_2$)$_b$R$^b$ wherein b is 0 or an integer from 1 to 3 and R$^b$ is an aromatic, heterocyclic or cyclical aliphatic group optionally substituted with one or more groups selected from lower alkyl, halogen, substituted alkyl, nitro, alkoxy, phenoxy, sulfonamido, carboxylic ester, or carboxamide;

R$^4$ is an aliphatic, aromatic, or heterocyclic group optionally substituted with or one or more polar groups, which polar group may be protected or unprotected;

R$^5$ is hydrogen, or an alkyl- or aryl-substituted ether, thioether, or amine; and E is —(CH$_2$)$_m$COR', —CO(CH$_2$)$_n$R', —C(O)C(O)R', or an olefin attached to an electron withdrawing group, wherein m and n are independently 0 or an integer from 1 to 6, wherein R' is independently halogen, cyano, alkyl, substituted alkyl, aryl, substituted aryl, heterocyclic group or substituted heterocyclic group, and wherein the substituted alkyl, substituted aryl and substituted heterocyclic group are independently substituted with halo, hydroxyl, thiol, nitro, amino, amido, alkoxy, haloalkoxy, alkylenedioxy, alkyl, haloalkyl, or hydroxyalkyl.

* * * * *